(12) United States Patent
Salas Pérez-Rasilla et al.

(10) Patent No.: US 11,814,673 B2
(45) Date of Patent: *Nov. 14, 2023

(54) CARDIOVASCULAR DISEASE

(75) Inventors: Eduardo Salas Pérez-Rasilla, Manchester (GB); Jaume Marrugat De La Iglesia, Barcelona (ES); Roberto Elosua Llanos, Barcelona (ES); Sergio Castillo Fernandez, Barcelona (ES); Joan Salgado Gomez, Barcelona (ES); José Maria Ordovás Munoz, Barcelona (ES)

(73) Assignee: GENinCode PLC, Manchester (GB)

( * ) Notice: Subject to any disclaimer, the term of this patent is extended or adjusted under 35 U.S.C. 154(b) by 640 days.

This patent is subject to a terminal disclaimer.

(21) Appl. No.: 14/236,932

(22) PCT Filed: Aug. 1, 2012

(86) PCT No.: PCT/EP2012/065020
§ 371 (c)(1),
(2), (4) Date: Jul. 28, 2014

(87) PCT Pub. No.: WO2013/020870
PCT Pub. Date: Feb. 14, 2013

(65) Prior Publication Data
US 2014/0342355 A1    Nov. 20, 2014

(30) Foreign Application Priority Data

Aug. 5, 2011 (EP) .................................... 11176695

(51) Int. Cl.
*C12Q 1/6827* (2018.01)
*C12Q 1/6883* (2018.01)
(Continued)

(52) U.S. Cl.
CPC ............. *C12Q 1/6827* (2013.01); *A61P 9/00* (2018.01); *C12Q 1/6883* (2013.01); *G16H 50/30* (2018.01);
(Continued)

(58) Field of Classification Search
CPC ...... A61P 9/00; C12Q 2600/112; G16H 50/30
See application file for complete search history.

(56) References Cited

U.S. PATENT DOCUMENTS

2005/0112611 A1    5/2005 Helgadottir

FOREIGN PATENT DOCUMENTS

CA         2679581 A1    8/2008
TJ    WO 2005/087953 A2    9/2005
(Continued)

OTHER PUBLICATIONS

Malarstig (Curr Atheroscler Rep, 2010, 12:159-166).*
(Continued)

*Primary Examiner* — Jesse P Frumkin
(74) *Attorney, Agent, or Firm* — Wolf, Greenfield & Sacks, P.C.

(57) ABSTRACT

The invention relates to a method for the reclassification of a subject to a more appropriate risk assessment to that obtained using the algorithms for such risk estimation such us but not limited to Framingham, Regicor, Score, Procamor Qrisk based on the presence of different polymorphisms. The invention also relates to a method for determining the risk of suffering a cardiovascular disease by combining the absence or presence of one or more polymorphic markers in a sample from the subject with conventional risk factors for CVD as well as computer-implemented means for carrying out said method.

13 Claims, 4 Drawing Sheets

Figure 1:
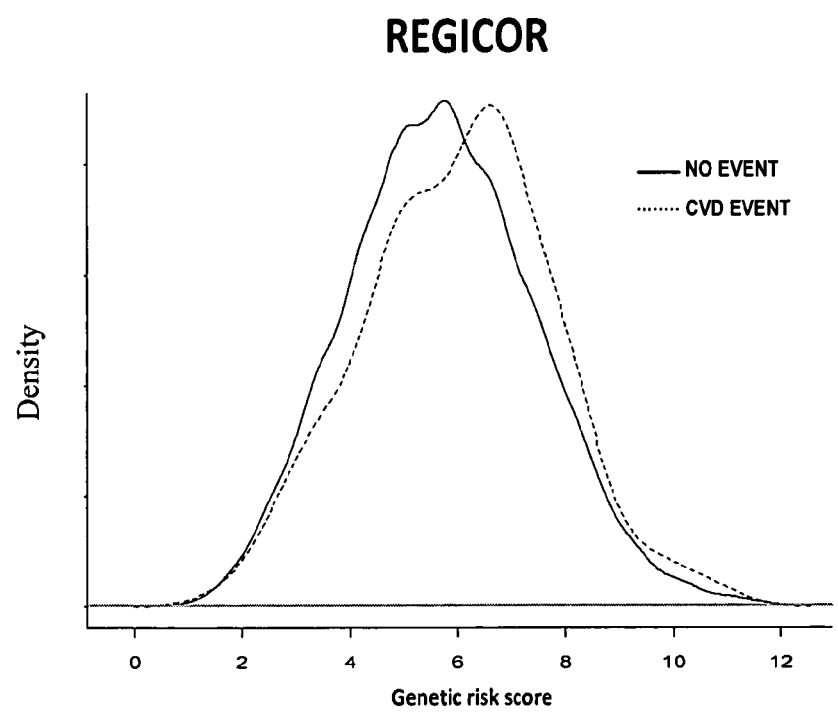
Figure 1:
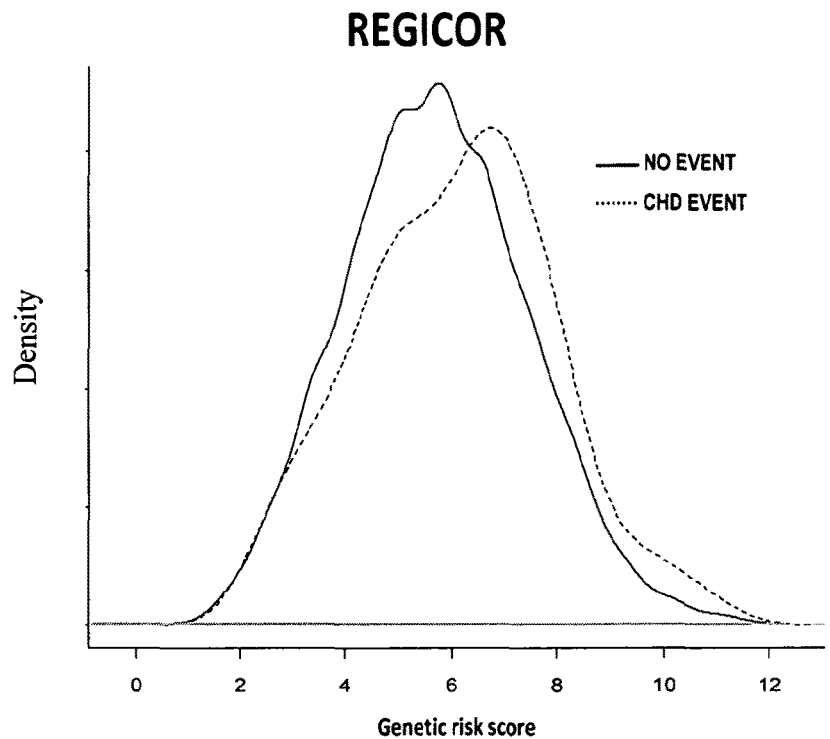

Specification includes a Sequence Listing.

REGICOR

|  | NO EVENT | CVD EVENT |  |
|---|---|---|---|
|  | N=2,634 | N=126 | P-value |
| Weighted genetic score (mean [SD]) | 5.72 (1.73) | 6.03 (1.74) | 0.047 |
| Coronary risk (95%CI) | 3.30 (1.69-5.97) | 7.56 (4.55-12.3) | <0.001 |
| Coronary risk + genetic score (95%CI) | 3.32 (1.64-6.06) | 7.70 (4.81-12.9) | <0.001 |

(51) Int. Cl.
*A61P 9/00* (2006.01)
*G16H 50/30* (2018.01)

(52) U.S. Cl.
CPC .. *C12Q 2600/112* (2013.01); *C12Q 2600/118* (2013.01); *C12Q 2600/156* (2013.01)

(56) References Cited

FOREIGN PATENT DOCUMENTS

| WO | WO 2008/102380 A1 | 8/2008 | |
|---|---|---|---|
| WO | WO 2010/113034 A2 | 10/2010 | |
| WO | WO 2010/142713 A1 | 12/2010 | |
| WO | WO-2011133418 A1 * | 10/2011 | ............. A61K 31/22 |

OTHER PUBLICATIONS

Kathiresan et al. (Nature Genetics 2009, vol. 41, pp. 334-341).*
Mega et al. (Circulation, 2009, 120:S1144).*
Peng (Clin Chem Lab Med 2009, 47(8): 917-922).*
Kumar (Crit Pathways in Cardiol, 2009, 8:104-111).*
Uchiyama et al. (J. Stroke and Cerebrovascular Disease, 2009, vol. 18, p. 482-490).*
Companioni (Rev Esp Cardiol, 2011 64(6): 509-514).*
[No Author Listed], Data Sheet Affymetrix® Genome-Wide Human SNP Array 6.0. 2007;1-4.
[No Author Listed], Illumina 1M Duo Bead Chip. Jan. 1, 2008. 1-3.
[No Author Listed], Illumina, Whole-genome expression analysis using the Sentrix Human-6 and HumanRef-8 expression beadchips. Jun. 28, 2005. 1-8.
Arking et al., Understanding cardiovascular disease through the lens of genome-wide association studies. Trends Genet. Sep. 2009;25(9):387-94. doi: 10.1016/j.tig.2009.07.007. Epub Aug. 26, 2009.
Clarke et al., Genetic variants associated with Lp(a) lipoprotein level and coronary disease. N Engl J Med. Dec. 24, 2009;361(26):2518-28. doi: 10.1056/NEJMoa0902604.
Hiura et al., Validation of the association of genetic variants on chromosome 9p21 and 1q41 with myocardial infarction in a Japanese population. Circ J. Aug. 2008;72(8):1213-7.
Linsel-Nitschke et al., Genetic variation in the arachidonate 5-lipoxygenase-activating protein (ALOX5AP) is associated with myocardial infarction in the German population. Clin Sci (Lond). Nov. 2008;115(10):309-15. doi: 10.1042/CS20070468.
Lluis-Ganella et al., Assessment of the value of a genetic risk score in improving the estimation of coronary risk. Atherosclerosis. Jun. 2012;222(2):456-63. doi: 10.1016/j.atherosclerosis.2012.03.024. Epub Mar. 30, 2012.
Mehta, A genome-wide association study in Europeans and South Asians identifies 5 new loci for coronary artery disease. Circ Cardiovasc Genet. Aug. 1, 2011;4(4):465-6. doi: 10.1161/CIRCGENETICS.111.960989.
Wang et al., Association of SNP rs17465637 on chromosome 1q41 and rs599839 on 1p13.3 with myocardial infarction in an American Caucasian population. Ann Hum Genet. Jul. 2011;75(4):475-82. doi: 10.1111/j.1469-1809.2011.00646.x. Epub Apr. 4, 2011.
Yan et al., Evaluation of population impact of candidate polymorphisms for coronary heart disease in the Framingham Heart Study Offspring Cohort. BMC Proc. Dec. 15, 2009;3 Suppl 7:S118.
Hlatky et al., Criteria for evaluation of novel markers of cardiovascular risk: a scientific statement from the American Heart Association. Circulation. May 5, 2009;119(17):2408-16. doi: 10.1161/CIRCULATIONAHA.109.192278. Epub Apr. 13, 2009. Erratum in: Circulation. Jun. 30, 2009;119(25):e606. Hong, Yuling [added].
Shmueli, To Explain or to Predict? Statistical Science. 2010;25(3):289-310. doi: 10.1214/10-STS330.

* cited by examiner

| | NO EVENT | CVD EVENT | |
|---|---|---|---|
| | N=2,634 | N=126 | P-value |
| Weighted genetic score (mean [SD]) | 5.72 (1.73) | 6.03 (1.74) | 0.047 |
| Coronary risk (95%CI) | 3.30 (1.69-5.97) | 7.56 (4.55-12.3) | <0.001 |
| Coronary risk + genetic score (95%CI) | 3.32 (1.64-6.06) | 7.70 (4.81-12.9) | <0.001 |

|  | NO EVENT | CHD EVENT |  |
|---|---|---|---|
|  | N=2,634 | N=89 | P-value |
| Weighted genetic score (mean [SD]) | 5.72 (1.73) | 6.11 (1.82) | 0.036 |
| Coronary risk (95%CI) | 3.30 (1.69-5.97) | 8.28 (4.89-12.4) | <0.001 |
| Coronary risk + genetic score (95%CI) | 3.32 (1.64-6.06) | 8.83 (5.78-13.7) | <0.001 |

Table 1

| SEQ ID NO: | Sequence comprising the polymorphism | dbSNP accession number | Allele of risk | Chrom. | Position in chrom. | Strand | Accession number/Build |
|---|---|---|---|---|---|---|---|
| 1 | ACCATAATAAGTTATGCTGAGAAGTTCTTTTTGTCATATGTGCAAGATAACAT | rs17455637 | C | 1 | 196042691 | + | AC_000044/03.03.2008 |
| 2 | GCTATCATTTAAATTCGTTGAAGACACAATATGCTGCTTGCACTTTCTATAAA | rs6725087 | C | 2 | 197498571 | + | AC_000045/03.03.2008 |
| 3 | CTGTGCTGCTTGGTGCCTCTGATATGAATACACTGACACGTCAAAGTAAC | rs9818870 | T | 3 | 136547031 | + | AC_000046/03.03.2008 |
| 4 | ACATCTGCCTCTCTAGACTATAAACTGTTGGGGCTGAGGTCTTCTTGTCTT | rs12526453 | C | 6 | 14155621 | + | AC_000049/03.03.2008 |
| 5 | TCATACTTACCCATATGATGACAGTTCAAAAGCAGCCACTCGGCAGAGCTAAG | rs1333049 | C | 9 | 22063860 | + | AC_000052/0.03.2008 |
| 6 | GAAGGGTAAAGGTGGTAGGATTGAGCCAGTGAGGCTGCCAGGCCAGAAACCTCTAGTTAG | rs1746048 | C | 10 | 44775824 | + | |
| 7 | GGCAAGTACCTGGCGACAGGGCTGCTCATGGCGTTGGACCTGGACAGTGGA | rs9982601 | T | 21 | 35599128 | + | AC_000064/03.03.2008 |
| 8 | TTCAGACACCTTGTTCTCAGAACCCAATGTGTTTATACAGGTTAGAGGAGAA | rs10455872 | G | 6 | 161010119 | + | |
| 9 | CTGACCTCAGGTGATCTGCCTGCCAGCCTCCCACAGTTTTGTGATTATAG | rs17216473* | A | 13 | 31303965 | + | |
| 10 | TGTCCAAGCGTCTCTTGCAATTCTAATTCTAATTAACCTCAATGTGCAACCATGA | rs105073951* | A | 13 | 31312096 | + | |
| 11 | CTCATGAACATGACTGTGAACAGGAAGAAGAACAAGCTTGGCCAA | rs9315051 | A | 13 | 31336177 | + | |
| 12 | GAGTTTCCTGCGGATGGTGGTCCTTTCGGTTTTTTTAAAATATTTTATTGA | rs17222842* | G | 13 | 31340117 | + | |
| 13 | ACAGTTTTTTACTGTAAGTCCAATAAATAATACTCATCTTTAAAAGACATC | rs6922269 | A | 6 | 152252985 | + | NC_000006/03.03.2008 |
| 14 | CACAGTGTCTTTGCCGTCATTGAACTGAGAACCTAAGTGCTGAGTGAGGACGC | rs17228212 | C | 15 | 67458639 | + | |
| 15 | GCATGCTCTGCACCGTGCAGCGCGGTGTGATAATGCATTGCTAATGCTTG | rs4769874 | G | 13 | 31326441 | + | |
| 16 | ATACAGTCCCATTCTGAGGACTGACAGTAAAGATTCAACATATGAATTTG | rs9315050* | A | 13 | 31336045 | + | |
| 17 | ACCTCACCAACCGAAGAGGAATTGCTAGATGAGAATCCTTCCCCGGAATTTC | rs8541863 | A | 13 | 31332547 | + | |
| 18 | GCTAGTGTCTCTTCCCGAGCCACTCGTTACCCAGTGCGCCTTACATATCATGG | rs17222814 | G | 13 | 31299553 | + | |
| 19 | GGGCTCCAAGAACAGACCTAGACGCCTAGCAGCCAACCTCCATGTGAAGAGTCCA | rs3798220 | C | 6 | 160961137 | + | |
| 20 | ACCAGATCTTGGAGTTGTCATCCCGCTTCAACAAGGCATGATCGCTCCAC | CD065 | T | 15 | 102238605 | + | |
| 21 | AGGAAGAAGCTGAAGTCAGGCACTTGAGGCCATGCTAGAACTACTTTTTCTGAAAACTTAGTG | rs17114036 | A | 1 | 569628821 | + | |
| 22 | ACCTCGCTTGCTTCTTAAGAACCTTCGAGCAGCTGAACCGGGATTGCAACCCCT | rs17609840 | G | 6 | 35034600 | + | |
| 23 | GCTAGTCTCTTAGAGAACTTCGGTGACTTCATCCACCTGTCTATTCATGCAT | rs12190287 | C | 6 | 134214525 | + | |
| 24 | TGGGCTAGGAGGCCTCCGAGCCTGCAGCGTAGGGAACTGGGAAGAGTCCA | rs11556924 | C | 7 | 129663496 | + | |
| 25 | TTTGCAACCGTCGGGCCTTTCAGCCGCATCCCACTGGGAACTTAAAATGTAGCCCTGAG | rs4773144 | G | 13 | 110961712 | + | |
| 26 | GGGCTAGGAGCCTAGACCCTACTACTTCGCCACTCGCTCCCTCGCTCTGCGAGGTGG | rs2895811 | C | 14 | 100133942 | + | |
| 27 | GGGCTTCCAGTTGCTACCCGAGCTGGAGTCGTGGAGGGAGCGTTGGGAGCCAGCG | rs3825807 | A | 15 | 79089111 | + | |
| 28 | TGCTGTTCAGACTTTGGCTTCTGAGGGAAGGATCAGTGGTTGACAAGAGGGA | rs216172 | C | 17 | 2126594 | - | |
| 29 | CCTAGGGCTGCAGCACCAAACACAGATGAATGACAACGAAATGAATGAAT | rs12936587 | G | 17 | 17543722 | + | |
| 30 | TTGTACTACCCAGCTCTTCTCCCCATCCGTGCTACTCTTGACATTAACTATGCT | rs46522 | T | 17 | 469988597 | - | |
| 31 | TCTCCAAACTGAAAATAAAAACAGTGAAAACAGAAAATATATTTCCTAAA | rs974819 | T | 11 | 1036060567 | - | |
| 32 | tgcacttccaaaaggggaacgtttgaAacagttactttactttccaatgccc | rs4380028 | C | 15 | 79111093 | + | |
| 33 | TTATGGGGTACCTAAGTAATTATGACAGCACAGCGAATAGAGATTACGAATTTGGACC | rs10853541 | C | 7 | 107244545 | + | |
| 34 | ATCTGTGCCTGGTCCAGTGCAGGCACGCAAACACAGTGTTAGGAAGG | rs2505083 | C | 10 | 30335122 | + | |

Figure 2

Table G. Description of the phenotype characteristics of the individuals included in the analysis from the REGICOR and from the Framingham Heart Study cohorts.

| | REGICOR | | | | | | Framingham | | | | | |
|---|---|---|---|---|---|---|---|---|---|---|---|---|
| | All | None | CHD | CVD | p-CHD | p-CVD | All | None | CHD | CVD | p-CHD | p-CVD |
| N | 2,760 | 2,634 | 80 | 126 | | | 3,557 | 2,563 | 429 | 674 | | |
| Age (years)* | 53.9 (11.1) | 53.6 (11.0) | 61.5 (9.9) | 61.2 (9.9) | <0.001 | <0.001 | 56.0 (9.3) | 54.8 (9.2) | 60.5 (7.8) | 61.2 (7.4) | <0.001 | <0.001 |
| Gender (male)† | 1,327 (48.1) | 1,249 (47.4) | 56 (62.9) | 78 (61.9) | 0.004 | 0.001 | 1,540 (43.5) | 1,190 (41.6) | 259 (58.3) | 350 (51.9) | <0.001 | <0.001 |
| SBP (mmHg)* | 133 (20.8) | 132 (20.5) | 147 (18.8) | 146 (21.2) | <0.001 | <0.001 | 127 (17.8) | 125 (17.4) | 134 (17.4) | 134 (18.0) | <0.001 | <0.001 |
| DBP (mmHg)* | 79.5 (10.3) | 79.4 (10.3) | 82.9 (10.4) | 82.7 (11.6) | 0.002 | 0.004 | 75.0 (9.8) | 74.6 (9.8) | 77.7 (9.6) | 76.6 (9.7) | <0.001 | <0.001 |
| Hypertension† | 1,187 (43.2) | 1,022 (38.9) | 65 (70.8) | 85 (68.0) | <0.001 | <0.001 | 1,121 (31.7) | 802 (28.0) | 214 (50.0) | 319 (47.5) | <0.001 | <0.001 |
| Smoking† | 616 (22.6) | 585 (22.5) | 24 (27.0) | 31 (24.6) | 0.320 | 0.878 | 713 (20.2) | 531 (18.5) | 111 (25.9) | 182 (27.0) | 0.002 | <0.001 |
| Total cholesterol (mg/dL)* | 226 (42.7) | 225 (42.2) | 239 (46.1) | 240 (51.3) | 0.003 | <0.001 | 210 (38.6) | 207 (37.4) | 224 (41.6) | 236 (39.3) | <0.001 | <0.001 |
| LDL cholesterol (mg/dL)* | 153 (38.7) | 152 (38.3) | 163 (39.8) | 165 (44.5) | 0.015 | 0.031 | 128 (34.0) | 124 (33.3) | 133 (33.7) | 135 (37.3) | 0.001 | <0.001 |
| HDL cholesterol (mg/dL)* | 52 (13.3) | 52 (13.3) | 44 (12.0) | 46 (12.2) | <0.001 | <0.001 | 51 (15.2) | 52 (15.3) | 46 (13.1) | 47 (14.1) | <0.001 | <0.001 |
| Triglycerides (mg/dL)‡ | 93 (71-130) | 92 (70-128) | 126 (94-174) | 119 (84-170) | <0.001 | <0.001 | 116 (83-172) | 112 (80-164) | 158 (104-217) | 157 (101-217) | <0.001 | <0.001 |
| Cholesterol treatment† | 184 (6.7) | 166 (6.3) | 13 (14.7) | 18 (14.4) | 0.002 | 0.061 | 166 (4.7) | 118 (4.1) | 28 (6.5) | 48 (7.1) | 0.035 | 0.001 |
| Diabetes† | 364 (14.2) | 351 (13.6) | 28 (31.8) | 33 (26.6) | <0.001 | <0.001 | 226 (6.4) | 138 (4.8) | 60 (14.0) | 88 (13.1) | <0.001 | <0.001 |
| Diabetes treatment† | 184 (9.8) | 169 (9.3) | 16 (35.6) | 17 (37.4) | <0.001 | <0.001 | 98 (2.8) | 48 (1.7) | 31 (7.2) | 42 (6.2) | <0.001 | <0.001 |
| Body mass index (kg/m²)* | 27.5 (4.5) | 27.4 (4.5) | 29.4 (4.9) | 29.4 (4.6) | <0.001 | <0.001 | 27.1 (4.8) | 27.0 (4.8) | 27.9 (4.4) | 27.9 (4.5) | <0.001 | <0.001 |
| Obesity (BMI≥30 kg/m²)† | 714 (26.1) | 664 (25.4) | 34 (38.3) | 50 (40.0) | 0.007 | <0.001 | 780 (22.1) | 604 (21.2) | 117 (27.3) | 176 (26.2) | 0.506 | 0.005 |
| Family history of CHD† | 324 (11.8) | 301 (11.5) | 17 (19.3) | 23 (18.4) | 0.026 | 0.020 | 551 (24.3%) | 478 (24.3%) | 55 (32.5%) | 73 (29.2%) | 0.016 | 0.008 |

CHD: individuals who presented a coronary event during the follow-up; CVD: individuals who presented a cardiovascular event (includes those with a coronary event); SBP: systolic blood pressure; DBP: diastolic blood pressure; LDL: low density lipoprotein; HDL: high density lipoprotein; BMI: body mass index; CI: confidence interval.

* mean (standard deviation); † n (proportion, %); ‡ median (25 and 75 percentiles); § mean (95% confidence interval).

Figure 3

SEQUENCE LISTING

```
<160> NUMBER OF SEQ ID NOS: 34

<210> SEQ ID NO 1
<211> LENGTH: 53
<212> TYPE: DNA
<213> ORGANISM: Homo sapiens

<400> SEQUENCE: 1
accataataa gttatgctga gaagttcttt tttgtcatag tgcaagataa cat            53

<210> SEQ ID NO 2
<211> LENGTH: 52
<212> TYPE: DNA
<213> ORGANISM: Homo sapiens

<400> SEQUENCE: 2
gctatcattt aaatttggtt gagacacaat atgctgttgc actttctata aa             52

<210> SEQ ID NO 3
<211> LENGTH: 52
<212> TYPE: DNA
<213> ORGANISM: Homo sapiens

<400> SEQUENCE: 3
ctgtgctgct tggtgcctct ctgatatgaa tacactgaca cgtcaaagta ac             52

<210> SEQ ID NO 4
<211> LENGTH: 52
<212> TYPE: DNA
<213> ORGANISM: Homo sapiens

<400> SEQUENCE: 4
acatctgcct ctctagacta taaactcttt ggggctaggt cttctttgtc tt             52

<210> SEQ ID NO 5
<211> LENGTH: 52
<212> TYPE: DNA
<213> ORGANISM: Homo sapiens

<400> SEQUENCE: 5
tcatactaac catatgatca acagttcaaa agcagccact cgcagagcta ag             52

<210> SEQ ID NO 6
<211> LENGTH: 53
<212> TYPE: DNA
<213> ORGANISM: Homo sapiens

<400> SEQUENCE: 6
```
gaagggtaaa gggtggtagg attgagcgag tcaggccaga aacctctagt tag        53

<210> SEQ ID NO 7
<211> LENGTH: 52
<212> TYPE: DNA
<213> ORGANISM: Homo sapiens

<400> SEQUENCE: 7
ggcaagtacc tgggcacagg gctgcttcat ggccttggac ctggacagtg ga        52

<210> SEQ ID NO 8
<211> LENGTH: 52
<212> TYPE: DNA
<213> ORGANISM: Homo sapiens

<400> SEQUENCE: 8
ttcagacacc ttgttctcag aacccaatgt gtttatacag gttagaggag aa        52

<210> SEQ ID NO 9
<211> LENGTH: 52
<212> TYPE: DNA
<213> ORGANISM: Homo sapiens

<400> SEQUENCE: 9
ctgacctcag gtgatctgcc tgcctcagcc tcccacagtt ttgtgattat ag        52

<210> SEQ ID NO 10
<211> LENGTH: 52
<212> TYPE: DNA
<213> ORGANISM: Homo sapiens

<400> SEQUENCE: 10
tgtccaagcc tctctttgca attctaatta acctcaatgt tgcaaccata ga        52

<210> SEQ ID NO 11
<211> LENGTH: 52
<212> TYPE: DNA
<213> ORGANISM: Homo sapiens

<400> SEQUENCE: 11
ctcatgaaca tgactgtgaa caggaaaaca gggagagaat gaagctggcc aa        52

<210> SEQ ID NO 12
<211> LENGTH: 52
<212> TYPE: DNA
<213> ORGANISM: Homo sapiens

<400> SEQUENCE: 12
gagttttcct gggatgtggt cctttcggtt ttttaaaaat tatttttatt ga        52

<210> SEQ ID NO 13
<211> LENGTH: 52
<212> TYPE: DNA
<213> ORGANISM: Homo sapiens

<400> SEQUENCE: 13
acagttttta ctgtaactgc caataaataa tactcatctt taaaaagaca tc        52

<210> SEQ ID NO 14
<211> LENGTH: 53
<212> TYPE: DNA
<213> ORGANISM: Homo sapiens

<400> SEQUENCE: 14
cacactgtct ttgccgtcat tgaactcgca acctaactgc tgagtgagga cac       53

<210> SEQ ID NO 15
<211> LENGTH: 52
<212> TYPE: DNA
<213> ORGANISM: Homo sapiens

<400> SEQUENCE: 15
gcatgctctg cacccgtgca gagcgcgtgt gataatgcat tgctaatgct tg        52

<210> SEQ ID NO 16
<211> LENGTH: 52
<212> TYPE: DNA
<213> ORGANISM: Homo sapiens

<400> SEQUENCE: 16
atacagtccc attctgagga actgagagta aagattcaac atatgaattt tg        52

<210> SEQ ID NO 17
<211> LENGTH: 52
<212> TYPE: DNA
<213> ORGANISM: Homo sapiens

<400> SEQUENCE: 17
acctcaccaa ccgaggagga attgctagat gagatccttc ccccggaatt tc        52

<210> SEQ ID NO 18
<211> LENGTH: 52
<212> TYPE: DNA
<213> ORGANISM: Homo sapiens

<400> SEQUENCE: 18
gctagtctct ttccccagcc actgttaccc agtgggctta catatatcat gg        52

<210> SEQ ID NO 19
<211> LENGTH: 52
<212> TYPE: DNA
<213> ORGANISM: Homo sapiens

<400> SEQUENCE: 19
ggctccaaga acagcctaga cacttctatt tcctgaacat gagattcgag gt        52

<210> SEQ ID NO 20
<211> LENGTH: 53
<212> TYPE: DNA
<213> ORGANISM: Homo sapiens

<400> SEQUENCE: 20
accagatctt cgagttgtca tcccccttc aagcaagggc atgatgcctc cac        53

<210> SEQ ID NO 21
<211> LENGTH: 52
<212> TYPE: DNA
<213> ORGANISM: Homo sapiens

<400> SEQUENCE: 21
agcaagagct gaagtcaggc agtggtaact acttttttcct gaaaacttag tg       52

<210> SEQ ID NO 22
<211> LENGTH: 52
<212> TYPE: DNA
<213> ORGANISM: Homo sapiens

```
<400> SEQUENCE: 22
aggtcctgct ttcttaagaa ccttgagcag ctgaaccggg attggaaccc ct            52

<210> SEQ ID NO 23
<211> LENGTH: 52
<212> TYPE: DNA
<213> ORGANISM: Homo sapiens

<400> SEQUENCE: 23
tctccaaggg ctgagaactt cggtgacttc atccacctgt ctatttgcac at            52

<210> SEQ ID NO 24
<211> LENGTH: 52
<212> TYPE: DNA
<213> ORGANISM: Homo sapiens

<400> SEQUENCE: 24
tggggctagc agcctctggc tcaggacggt caacaggact ggaagagtcc ca            52

<210> SEQ ID NO 25
<211> LENGTH: 52
<212> TYPE: DNA
<213> ORGANISM: Homo sapiens

<400> SEQUENCE: 25
tttgcaagcg tcggcctttc acgggaactg ggaacttaaa atgtagcctg ag            52

<210> SEQ ID NO 26
<211> LENGTH: 52
<212> TYPE: DNA
<213> ORGANISM: Homo sapiens

<400> SEQUENCE: 26
ggggctagga cctacactcc agccacgta ctctgctcct gcctgggagg tg             52

<210> SEQ ID NO 27
<211> LENGTH: 52
<212> TYPE: DNA
<213> ORGANISM: Homo sapiens

<400> SEQUENCE: 27
ggcctccagt gtacccagag ctggagtctc gacgggagcg ttgggagcag cg            52

<210> SEQ ID NO 28
<211> LENGTH: 52
<212> TYPE: DNA
<213> ORGANISM: Homo sapiens

<400> SEQUENCE: 28
tgctgttcac actttggctt ctgagggaag gatcagtggt tgaaagaggg ga            52

<210> SEQ ID NO 29
<211> LENGTH: 52
<212> TYPE: DNA
<213> ORGANISM: Homo sapiens

<400> SEQUENCE: 29
cctagggctc acagcaccaa acacagattg aatgcacaac gaatgaatga at            52

<210> SEQ ID NO 30
<211> LENGTH: 52
<212> TYPE: DNA
<213> ORGANISM: Homo sapiens
```

```
<400> SEQUENCE: 30
ttgtactacc cagctcttcc cccatcccgt tactcttgac attaactatg ct          52

<210> SEQ ID NO 31
<211> LENGTH: 52
<212> TYPE: DNA
<213> ORGANISM: Homo sapiens

<400> SEQUENCE: 31
tctccaaaca tgaaaataaa acagtagaaa cagaaaaata tatttcctta aa          52

<210> SEQ ID NO 32
<211> LENGTH: 52
<212> TYPE: DNA
<213> ORGANISM: Homo sapiens

<400> SEQUENCE: 32
cgacacttcc aaatgtggga cgttggacaa gttacttaac ctttccatgc cc          52

<210> SEQ ID NO 33
<211> LENGTH: 52
<212> TYPE: DNA
<213> ORGANISM: Homo sapiens

<400> SEQUENCE: 33
ttatgggtac ctaagtatta gcagcacgca atagagatac tagatttgga cc          52

<210> SEQ ID NO 34
<211> LENGTH: 52
<212> TYPE: DNA
<213> ORGANISM: Homo sapiens

<400> SEQUENCE: 34
atctgtgcct ggtcccagtg cagcaccaaa ggcaaacaca gtgttaggaa gg          52
```

CARDIOVASCULAR DISEASE

RELATED APPLICATION

This application is a national stage filing under 35 U.S.C. § 371 of international application PCT/EP2012/065020, filed Aug. 1, 2012, which was published under PCT Article 21(2) in English, the disclosure of which is incorporated by reference herein in its entirety.

FIELD OF THE INVENTION

The present invention relates to the field of cardiovascular diseases or disorders. More specifically, it relates to markers and methods for determining whether a subject, particularly a human subject, is at risk of developing a cardiovascular disease or disorder, developing a cardiovascular event, having a cardiovascular disease or disorder, or experiencing a complication of a cardiovascular disease.

TECHNICAL BACKGROUND

Cardiovascular disease (CVD) is a term for heart and blood vessel diseases, including—among others—ischemic heart disease (being the most common type of CVD in the industrialized countries; this disorder refers to problems with the circulation of the blood to the heart muscle), cerebrovascular disease (refers to problems with the circulation of the blood in the blood vessels of the brain), and peripheral vascular disease (affecting the circulation primarily in the legs). Subjects with CVD may develop a number of complications (hereinafter referred to as CVD complications) including, but not limited to, fatal or non-fatal myocardial infarction, stroke, angina pectoris, transient ischemic attacks, and peripheral arteriopathy.

At the beginning of the twentieth century, cardiovascular disease was responsible for 10% of all deaths worldwide. Nowadays, it represents about 30% of all deaths and 80% of these deaths occur in developing countries. Cardiovascular disease is the leading cause of death in the USA, and Europe. Cardiovascular disease, besides being the leading cause of death, is a highly prevalent disease which causes high health care costs.

From the point of view of public health, the policy to be developed in relation to cardiovascular disease should seek to reduce the population's risk of developing cardiovascular disease (World Health Organization. The World Health Report 2004—Changing History. Geneva: World Health Organization; 2004). To this avail, the stratification of the population in relation to its cardiovascular risk would allow the establishment of preventive measures to prevent or delay the onset of the disease. Stratification would also help in establishing a treatment for the afflicted subjects by improving efficiency (avoiding the occurrence of cardiovascular events and complications) and cost-effectiveness (World Health Organization. World Health Report 2004—Changing History. Geneva: World Health Organization; 2004; Bakhai A. The burden of coronary, cerebrovascular and peripheral arterial disease. PharmacoEconomics 2004;22 (Suppl 4):11-18.).

Since the *Framingham Heart Study* (Wilson P W F, D'Agostino R B, Levy D, et al. Circulation 1988;97:1837-1847; Grundy Sm, Balady Gj, Criqui M H, et al. Circulation 1988;97:1876-1887) the existence of risk factors such as dyslipidemia (mainly the elevation of LDL-cholesterol), hypertension, diabetes, consumption of tobacco and sedentary lifestyle that are direct causes of coronary disease is well accepted. These risk factors are common in the population and the INTERHEART study has shown that they are universal, which means that these risk factors are the same in almost every geographic region and every racial/ethnic group worldwide, they are also consistent in men and women.

The identification of these risk factors has allowed the scientists to develop preventive and therapeutic strategies. Different studies (Sanz G. Fuster V. Nat Clin Pract Cardiovasc Med 2009;2:101-110) among others, the WHO MONICA (Monitoring trends and determinants in cardiovascular disease) (WHO MONICA Project Principal Investigators. J Clin Epidemiol. 1988;41:105-14) and the ARIC study (Atherosclerosis Risk in Communities) (Rosamond W D, Chambless L E, Folsom A, et al. N Engl J Med. 1998;339:861-7) have proven these to be effective measures.

In the nineties, the concept was developed that the intensity of the preventive-treatment measures against the risk factors should be adjusted to the severity of the risk (Grundy Sc, Bazzarre T, Cleeman J, et al. Circulation 2000;101:e3-e11). This concept was first proposed in the *Adult Treatment Panel Report of the National Cholesterol Education Program* (NCEP) and confirmed in its second report. A similar approach was proposed at the joint recommendation of the *European Society of Cardiology, European Society Artheriosclersosis and European Society of Hypertension* (Word D, De Backer G, Faergeman O, Gram I, Mancia G, Pyorala K. Atherosclerosis 1998;140:199-270). The adequacy of the measures against the risk is important because these are an important tool to achieve a proper balance between efficacy, safety and cost of therapy.

Before this invention, as described hereinafter, physicians estimated the patient's five- and ten-year cardiovascular disease risk based on multivariable regression equations derived from the Framingham cohorts in which the levels of traditional risk factors (age, total cholesterol, high-density-lipoprotein cholesterol, systolic blood pressure, smoking status) are assigned weights (points) to predict coronary heart disease (CHD) events, separately for men and women (Grundy Sm, Balady Gj, Criqui M H, et al. Circulation 1988;97:1876-1887). The calculated risk score was then converted into an absolute probability of developing CHD within that time frame.

Various scales/methods for cardiovascular risk estimation in Europe have been developed: the Prospective Cardiovascular Munster (PROCAM) scale, which estimates the risk of cardiovascular complications, the European Systematic Coronary Risk Evaluation (SCORE) Project which estimates the risk of cardiovascular death and the Registre Gironi del Cor [A heart registry undertaken in Girona] (REGICOR) that estimates the risk of myocardial infarction or angina.

While recognizing the usefulness of the scales/methods for calculating cardiovascular risk and despite all the efforts in the estimation of the cardiovascular risk in all patients (Greenland P, et al. Circulation 2001;104:1863-1867), a significant number of cardiovascular events occur in asymptomatic patients with a calculated "intermediate" risk using the tools nowadays in use for cardiovascular risk estimation (Greenland P, et al. Circulation 2001;104:1863-1867, Smith S C Jr. Am J Cardiol 2006;97 [Suppl]:28A-32A, Marrugat J, et al. J Epidemiol Community Health 2007;61:40-47).

Therefore, subjects with intermediate cardiovascular risk would benefit most from the use of tests that would allow a more precise risk stratification. Moreover, if these tests were feasible, practical and effective for a more precise definition of the cardiovascular risk and/or motivation for an effective change towards a healthy cardiovascular life-style (Greenland P, et al. Circulation 2001;104:1863-1867, Smith S C Jr. Am J Cardiol 2006:97 [Suppl]:28A-32A), this would mean a significant improvement over the present situation.

Several strategies have been followed to solve this limitation of the scales/methods nowadays in use to calculate the cardiovascular risk.

In recent years various studies have evaluated whether the addition of information on emerging risk factors such as those described by Wang improve the predictive capability, but the results have been discouraging (Wang T J, Gona P, Larson M G, et al. N Engl J Med. 2006;355(25):2631-9).

An additional source of information that can improve the predictive capability of the algorithms for cardiovascular risk calculation is the individual genetic variability. It is well-known that there is a familial aggregation in the occurrence of cardiovascular disease suggesting the presence of genetic factors that modulate individual susceptibility. In recent years, it has been estimated that the inheritability (proportion of phenotypic variability attributable to genes) of ischemic heart disease mortality is from 0.53 to 0.57 and that for the onset of a heart attack is 0.56

It is also known that ischemic heart disease is not related to a single gene but to many genes that determine individual genetic susceptibility. In this context, coronary heart disease is defined as a complex disease that involves multiple genes, multiple genetic variants in each of these genes and environmental factors, with complex interactions between what will ultimately determine the individual susceptibility to this disease.

Recent technological advances have allowed the publication of the human genome sequence, the availability of public databases with millions of polymorphisms (SNPs), the improvement of the genotyping methods with a reduction of the analytical cost, and the knowledge of the patterns of linkage disequilibrium in the human genome. As a result of all these achievements, there is an increased interest and opportunities for studying the genetics of even complex diseases.

However, the identification and selection of genetic markers to constitute such a specific combination that will actually improve cardiovascular risk prediction is not an easy task. Several attempts have been made. There are already some cohort studies that have included a genetic variant on chromosome 9p21 in the risk functions, but without observing a significant improvement in the ability of discrimination of predictive models (Paynter N P, Chassman D I, Paimen J, et al. Ann Intern Med 2009;150:65-72). Other studies have included a genetic risk score based on the number of risk alleles accumulated in an individual in order to increase the magnitude of the observed association. Morrison et al (Morrison A C, et al. Am J Epidemiol 2007;166:28-35) compared the area under the receiver operating characteristic curve (ROC) using the cardiovascular risk score developed by members of the Atherosclerosis Risk in Communities study (ACRS) versus the area obtained by combining the score with the genetic ACRS Risk Score (GRS). The area under the curve were slight but not significantly increased both in the white population from 0.764 to 0.769 (ACRS versus ACRS+GRS) and from 0.758 to 0.769 in the black population.

Therefore, although several attempts have been made to solve the above-described limitation of the scales/methods nowadays in use to calculate the cardiovascular risk, this goal has not yet been accomplished.

Accordingly, there is a need for novel markers, including new genetic markers and specific combinations thereof that would successfully and advantageously predict who, especially of those predicted to have a moderate or intermediate risk in accordance to the scales/methods nowadays in use is, in truth, at higher risk of developing cardiovascular disease and/or cardiovascular disease complications such as—but not limited to—fatal or non-fatal myocardial infarction or angina pectoris or transient ischemic attack or stroke or peripheral arteriopathy in a way that preventive measures could be implemented to keep that risk at the lowest possible level.

Apart from the subjects classified to be at moderate risk, there is another group of subjects where the scales/methods nowadays in use are unable to provide a good estimation of their cardiovascular risk; young people (men <45 years and women <65) because due to their youth they are given a low cardiovascular risk, independent of the presence of classical cardiovascular risk factors in the subjects (Cooney M T, Dudita A L, Graham I M. J Am Coll Cardiol 2009;54:1209-1227).

Therefore, despite several attempts to solve the above-described limitation of the scales/methods nowadays in use to calculate the cardiovascular risk, this goal has not yet been accomplished.

Accordingly, there is also a need for novel markers, including new genetic markers and combinations thereof that could successfully and advantageously predict who is at a higher risk of developing cardiovascular disease and/or cardiovascular disease complications such as—but not limited to—fatal or non-fatal myocardial infarction or angina pectoris or stroke or transient ischemic attack or peripheral arteriopathy in young people, in a way that preventive measures could be implemented to keep that risk at the lowest possible level.

SUMMARY OF THE INVENTION

In a first aspect, the invention provides a method which is suitable to solve the limitations of the scales/methods nowadays in use to calculate the cardiovascular risk, namely that a significant number of cardiovascular events occur in patients with a calculated intermediate risk using the tools nowadays in use for cardiovascular risk estimation and that the cardiovascular risk estimation is inaccurate in young subjects.

The method provided according to the present invention solves the above mentioned limitations by improved cardiovascular risk assessment or by the (re)classification of the subject to a (more appropriate) risk status of having a cardiovascular disease or disorder and/or complications such as—but not limited to—fatal- or non-fatal myocardial infarction, angina pectoris, stroke and/or peripheral arteriopathy compared to the methods nowadays in use and comprising the steps of determining in a sample isolated from said subject the presence in at least one allele of polymorphisms at positions 27 within the nucleic acid sequences of SEQ ID NO:1 to 34, wherein the presence at position 27 of a C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO:12, A in SEQ ID NO:13, C in SEQ ID NO:14, G in SEQ ID NO:15, A in SEQ ID NO:16, A in SEQ ID NO:17, G in SEQ ID NO:18, C in SEQ ID NO:19, T in SEQ ID NO:20 A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID NO:31, C in SEQ ID NO:32, C in SEQ ID NO:33, and/or C in SEQ ID NO:34 is indicative of a risk of suffering a cardiovascular event (fatal or non-fatal acute myocardial infarction, or angina pectoris, or stroke, or transient ischemic attack, or peripheral arteriopathy) in the next ten years, which is better than the risk assessment done by the scales/methods nowadays in use considering the classical risk factors alone.

"Improved cardiovascular risk assessment" in the context of this application should be understood as a prediction of the probability to develop a cardiovascular event that fits better than the risk assessment done by scales/methods nowadays in use, such as but not limited to Framingham risk score, adapted Framingham risk score (such but not limited to Regicor), Score, HeartScore, Procam, Reynolds, and QRisk, with the number of events that a particular patient has suffered (within the context of a retrospective study) or will suffer. The improvement can be measured as an increase in the area under the ROC curve, or as a higher c statistic value as e.g. measured by computing the concordance index using the rcorr.cens function from the R-package H-misc., "Improved cardiovascular risk assessment" in the context of this application is used interchangeably with "refined cardiovascular risk assessment".

"(Re)classification of the subject to a (more appropriate) risk status" in the context of this application should be understood as a more accurately stratification of the individual into a higher or lower risk categories of clinical importance as defined by Nancy R. Cook (Cook N R. Use and misuse of the receiver operating characteristic curve in risk prediction. Circulation 2007;115:928-935. The goodness of the (reClassification can be measured by the net reclassification improvement (Pencina M J, D'Agostino R B, Sr., Steyerberg E W. Extensions of net reclassification improvement calculations to measure usefulness of new biomarkers. StatMed. 2011;486 30(1):11-21, which is included herein by reference in its entirety), and/or by the integrated discrimination improvement (Chambless L E, Cummiskey C P, Cui G. Several methods to assess improvement in risk prediction models: Extension to survival analysis. Stat Med. 2011;30(1):22-38, which is included herein by reference in its entirety).

To calculate the 10-year expected number of events in each risk category and in each cohort, the Kaplan-Meier estimates can be used. Steyerberg E W, Pencina M J. Reclassification calculations for persons with incomplete follow-up. Ann Intern. Med. 2010;152(3):195-196, which is included herein by reference in its entirety. To assess the goodness-of-fit of the models, a version of the Hosmer-173 Lemeshow test can be used. See also D'Agostino R B, Nam B H. Evaluation of the Performance of Survival Analysis Models: Discrimination and Calibration Measures. Handbook of Statistics, 2003:Vol.23:1-25, which is included herein by reference in its entirety and Newson R. Confidence intervals for rank statistics: Somers' D and extensions. StataJournal, 2006;6:309-334, which is included herein by reference in its entirety.

Any one of the present methods, as described throughout this application, are in a preferred embodiment carried out ex vivo.

In a preferred embodiment the presence of the following alleles of polymorphisms is determined: polymorphisms at positions 27 within specific nucleic acid sequences, in particular the presence at position 27 of a C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, G in SEQ ID NO:12, and A in SEQ ID NO:16.

In a preferred embodiment the presence of the following alleles of polymorphisms is determined: polymorphisms at positions 27 within specific nucleic acid sequences, in particular the presence at position 27 of a C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, and A in SEQ ID NO:9, T in SEQ ID NO:10, G in SEQ ID NO:12, and A in SEQ ID NO:16, the latter four of them forming the haplotype B ALOX5AP and being considered as one risk genetic component in addition to the other 8 sequences.

In a preferred embodiment the presence of the following alleles of polymorphisms is determined: polymorphisms at positions 27 within the specific nucleic acid sequences, in particular the presence at position 27 of a C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, and G in SEQ ID NO:8.

In a preferred embodiment the presence of the following alleles of polymorphisms is determined: polymorphisms at positions 27 within the specific nucleic acid sequences, in particular the presence at position 27 of a C in SEQ ID NO:2, T in SEQ ID NO:3, C in SEQ ID NO:5, and G in SEQ ID NO:8.

These embodiments, i.e. specific combinations of SNPs are preferred embodiments of all aspects of this invention described below.

In another aspect, the invention relates to methods for the reclassification of the probability of an individual of presenting a fatal or non-fatal myocardial infarction, or angina, or stroke, or transient ischemic attack or peripheral arteriopathy in a ten year period and/or long-life period based on the presence of one or more of the polymorphisms mentioned above in combination with one or more conventional risk factors, wherein the relative contribution of the polymorphisms is given as a genetic score risk.

"Cardiovascular event" in the context of this application is used interchangeably with "cardiovascular complication, disease or disorder".

"AHA" in the context of this application should be understood as American Heart Association.

"GWAS" in the context of this application should be understood as genome-wide association studies.

The term "disease" and "disorder" shall be interpreted in the context of this application interchangeably.

In another aspect, the invention relates to methods for the reclassification of the probability of an individual classified as having a moderate risk to suffer a cardiovascular event (fatal or non-fatal myocardial infarction, or angina, or stroke, or transient ischemic attack or peripheral arteriopathy) in a ten year period and/or long-life period according to the methods nowadays in use based on the presence of one or more of the polymorphisms mentioned above in combination with one or more conventional risk factors, wherein the relative contribution of the polymorphisms is given as a genetic score risk.

In another aspect, the invention relates to methods for the reclassification of the probability of a young individual to suffer a cardiovascular event (fatal or non-fatal myocardial infarction, or angina, or stroke, or transient ischemic attack or peripheral arteriopathy) in a ten year period and/or long-life period calculated according to the methods nowadays in use based on the presence of one or more of the polymorphisms mentioned above in combination with one or more conventional risk factors, wherein the relative contribution of the polymorphisms is given as a genetic score risk.

In further aspects, the invention relates to methods for the determination of the probability of an individual of presenting a fatal or non-fatal myocardial infarction or angina pectoris or stroke or transient ischemic attack or peripheral arteriopathy in a ten year period or in a long-life period based on the presence of one or more of the polymorphisms mentioned above in combination with one or more conventional risk factors, wherein the relative contribution of the polymorphisms is given as a genetic score risk.

In further aspects, the invention relates to methods for the determination of the probability of an young individual of presenting a fatal or non-fatal myocardial infarction or angina pectoris or stroke or transient ischemic attack or peripheral arteriopathy in a 10 year period or in a long-life period based on the presence of one or more of the polymorphisms mentioned above in combination with one or more conventional risk factors, wherein the relative contribution of the polymorphisms is given as a genetic score risk.

In a further aspect, the invention relates to a computer program or a computer-readable media containing means for carrying out any of the methods of the invention.

In yet a further aspect, the invention relates to a kit comprising reagents for detecting the identity of the nucleotide at position 27 within a nucleic acid sequence selected from the group of SEQ ID NO:1 to 34.

In yet a further aspect, the invention relates to a kit comprising reagents for detecting the identity of the nucleotide at position 27 within a nucleic acid sequence selected from the group of SEQ ID NO:1, 2, 3, 4, 5, 6, 7, 8, 9, 10, 12, and 16.

In yet a further aspect, the invention relates to a kit comprising reagents for detecting the identity of the nucleotide at position 27 within a nucleic acid sequence selected from the group of SEQ ID NO:1, 2, 3, 4, 5, 6, 7, 8, and the following SEQ ID NO: 9, 10, 12, and 16 being considered as haplotype B ALOX5AP and the alleles AAAG in those sequences being considered as a single risk allele.

In yet a further aspect, the invention relates to a kit comprising reagents for detecting the identity of the nucleotide at position 27 within a nucleic acid sequence selected from the group of SEQ ID NO:1, 2, 3, 4, 5, 6, 7, and 8.

In yet a further aspect, the invention relates to a kit comprising reagents for detecting the identity of the nucleotide at position 27 within a nucleic acid sequence selected from the group of SEQ ID NO:2, 3, 5, and 8.

DETAILED DESCRIPTION OF THE INVENTION

The present invention is also further explained by the following Figures:

FIG. 1: REGICOR CVD analysis, genetic risk score, incidence of cardiovascular (a) and coronary (b) events.

FIG. 2: Table 1—summary of SNPs

FIG. 3: Table G—Phenotypic characteristics of participants

The authors of the present invention have solved two problems identified above in the scales/methods in use nowadays for the calculation of the risk in a subject to develop cardiovascular disease, cardiovascular events and cardiovascular complications including, but not limited to, fatal- and non-fatal myocardial infarction, stroke, angina pectoris, transient ischemic attacks, and peripheral arteriopathy.

The present application thus also pertains to a method for solving the limitation of the scales/methods by which a significant number of cardiovascular events occur in subjects with a calculated intermediate risk using the tolls nowadays in use for cardiovascular risk estimation and/or for solving the limitation of the scales/methods by which young subjects obtain an unrealistic low cardiovascular risk.

The present application solves the above-described limitation of the scales/methods used nowadays to calculate the cardiovascular risk by providing a method to reclassify the patients to a more appropriate risk status. A particular combination (as described above) of genetic markers is used, especially the combination as listed in table 1 (see FIG. 2), selected and evaluated by the inventors after a complex and genuine analysis of thousands of possible markers. Of the different possibilities to construct a genetic risk score (GRS), the inventors have been successful to identify a particular one, whereby this combination provided the best possible results. To calculate the genetic risk punctuation, the accumulated number of risk allele risk from those SNPs listed in table 1 that are present in each individual is considered. For each of the variants studied, every individual can have 0, 1 or 2 alleles of risk. On having calculated the summatory of risk alleles accumulated in the different set of the selected variants (n=34, 12, 9, 8, or 4), for each individual a score that could go from 0 to 68, 24, 18, 16, or 8, respectively was given. The inventors have generated new algorithms for cardiovascular risk estimation. This innovative strategy allows the reclassification of the patients with excellent net reclassification improvement values.

1. A method for a cardiovascular risk assessment in a subject comprising the steps of determining in a sample isolated from said subject the presence of polymorphisms at positions 27 within the nucleic acid sequences of SEQ ID NO:1 to 34, wherein the presence at position 27 of a C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO:12, A in SEQ ID NO:13, C in SEQ ID NO:14, G in SEQ ID NO:15, A in SEQ ID NO:16, A in SEQ ID NO:17, G in SEQ ID NO:18, C in SEQ ID NO:19, T in SEQ ID NO:20, A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID NO:31, C in SEQ ID NO:32, C in SEQ ID NO:33, and/or C in SEQ ID NO:34 is indicative of a risk of having a cardiovascular event.

2. A method for a reclassification of a subject to an improved risk assessment compared to that obtained using the scales/methods for such risk estimation such as, but not limited to Framingham, Regicor, Score, Procamor Qrisk comprising the steps of determining in a sample isolated from said subject the presence of polymorphisms at positions 27 within the nucleic acid sequences of SEQ ID NO:1 to 34, wherein the presence at position 27 of a C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO:12, A in SEQ ID NO:13, C in SEQ ID NO:14, G in SEQ ID NO:15, A in SEQ ID NO:16, A in SEQ ID NO:17, G in SEQ ID NO:18, C in SEQ ID NO:19, T in SEQ ID NO:20, A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID NO:31, C in SEQ ID NO:32, C in SEQ ID NO:33, and/or C in SEQ ID NO:34 is indicative of a risk of having a cardiovascular event.

3. A method for identifying a subject in need of cardiovascular therapy or in need of preventive cardiovascular therapy/measurements for a cardiovascular event comprising the steps of determining in a sample isolated from said subject the presence in at least one allele of polymorphisms at positions 27 within the nucleic acid sequences of SEQ ID NO:1 to 34, wherein the presence at position 27 of a C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO:12, A in SEQ ID NO:13, C in SEQ ID NO:14, G in SEQ ID NO:15, A in SEQ ID NO:16, A in SEQ ID NO: 17, G in SEQ ID NO:18, C in SEQ ID NO:19, T in SEQ ID NO:20, A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID NO:31, C in SEQ ID NO:32, C in SEQ ID NO:33, and/or C in SEQ ID NO:34 is indicative of having a decreased response to a cardiovascular therapy or of being in need of early and aggressive cardiovascular therapy or in need of prophylactic cardiovascular treatment.

4. A method to establish the therapeutical objectives of preventive and/or therapeutical treatments for a patient having a cardiovascular event or suspected of having a predisposition for a cardiovascular event wherein the patient and/or the therapeutical objectives are selected for said therapy based on the presence in a sample isolated from said subject of a polymorphism at position 27 in the nucleotide sequences of SEQ ID NO:1 to 34, wherein said polymorphism at said position 27 is C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO: 12, A in SEQ ID NO:13, C in SEQ ID NO:14, G in SEQ ID NO:15, A in SEQ ID NO:16, A in SEQ ID NO:17, G in SEQ ID NO:18, C in SEQ ID NO:19, T in SEQ ID NO:20, A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID N0:31, C in SEQ ID NO:32, C in SEQ ID NO:33, and/or C in SEQ ID NO:34.

5. A method of determining the probability of an individual of presenting a fatal or non-fatal myocardial infarction or angina in a 10 year period based on the presence of 1 to P classical risk factors and 1 to J polymorphisms at positions 27 in the nucleotide sequences of SEQ ID NO:1 to 34, wherein said polymorphisms at said positions 27 are selected from the group of C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO:12, A in SEQ ID NO:13, C in SEQ ID NO:14, G in SEQ ID NO:15, A in SEQ ID NO:16, A in SEQ ID NO:17, G in SEQ ID NO:18, C in SEQ ID NO:19, T in SEQ ID NO:20, A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID NO:31, C in SEQ ID NO:32, C in SEQ ID NO:33, and/or C in SEQ ID NO:34 using the formula:

$$1 - \hat{S}^{\exp\left[\frac{\sum_{p=1}^{P} \beta_{CRF_p} * CRF_{p,i} + \sum_{j=1}^{J} \beta_{SNP_j} * SNP_{j,i} -}{\sum_{p=1}^{P} \beta_{CRF_p} * \overline{CRF_p} - \sum_{j=1}^{J} \beta_{SNP_j} * \overline{SNP_j}}\right]}$$

wherein, $\hat{S}$ is the mean survival free of coronary events at the population, $$\sum_{p=1}^{P}$$

is the summatory function along the P classical risk factors, $\beta_{CRF_p}$ is the logarithm of hazard ratio corresponding to the classical coronary risk factor "p" as shown in table A, $CRF_{p,i}$ is the value of each coronary risk factor "p" included in the equation for an individual "i", $$\sum_{j=1}^{J}$$

is the summatory function along the J genetic variants.

$\beta_{SNP_j}$ is the logarithm of hazard ratio corresponding to the genetic variant "j" as shown in table B.

$SNP_{j,i}$ is the number of risk alleles (0,1,2) for a specific genetic variant "j" included in the equation for an individual "i".

$\overline{CRF_p}$ is the average value for the classical risk factor "p" in the population.

$\overline{SNP_j}$ is the average risk allele number of copies for genetic variant "j" in the population.

6. A method of determining the probability of an individual of presenting a fatal or non-fatal myocardial infarction or angina in a 10 year period based on the presence of 1 to P different classical risk factors and 1 to Q different genetic variants wherein said genetic variant is a polymorphism at positions 27 in the nucleotide sequences of SEQ ID NO:1 to 34, wherein said polymorphism at said position 27 are selected from the group of C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO:12, A in SEQ ID NO: 13, C in SEQ ID NO:14, G in SEQ ID NO:15, A in SEQ ID NO:16, A in SEQ ID NO:17, G in SEQ ID NO:18, C in SEQ ID NO:19, T in SEQ ID NO:20, A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID NO:31, C in SEQ ID NO:32, C in SEQ ID NO:33, and/or C in SEQ ID NO:34 using the formula:

$$1 - \hat{S}^{\exp\left[\frac{\Sigma_{p=1}^{P} \beta_{CRF_p} * CRF_{p,i} + \beta_{GRS} * GRS_i - \Sigma_{p=1}^{P} \beta_{CRF_p} *}{\overline{CRF_p} - \beta_{GRS} * \overline{GRS}}\right]},$$

wherein
  $\hat{S}$: mean survival free of coronary events at the population.
  exp: natural exponentiation.

$$\sum_{p=1}^{P} \beta_{CRF_p} * CRF_{p,i}:$$

where
  a.

$$\sum_{p=1}^{P}$$

summatory function along the P classical risk factors.
  b. $\beta_{CRF_p}$ logarithm of hazard ratio corresponding to the classical coronary risk factor "p". The values of the β for each coronary risk factor "p" are shown in table C.
  c. $CRF_{p,i}$: value of each coronary risk factor "p" included in the equation for an individual "i".
  $\beta_{GRS}$: logarithm of hazard ratio corresponding to one unit increase in the value of the genetic risk score. The value of this $\beta_{GRS}$ is 0.104 with a range of values going from 0.010 to 0.500.
  $\overline{CRF_p}$: average value for the classical risk factor "p" in the population. This average value will be adapted to the regional or national prevalence.
  $\overline{GRS}$: mean value of the genetic risk score in the population.

7. A method of determining the probability of an individual of presenting a fatal or non-fatal myocardial infarction or angina in a 10 year period based on the presence of 1 to P different classical risk factors and 1 to Q different genetic variants wherein said genetic variant is a polymorphism at positions 27 in the nucleotide sequences of SEQ ID NO:1 to 34, wherein said polymorphism at said position 27 is selected from the group of C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO:12, A in SEQ ID NO:13, C in SEQ ID NO:14, G in SEQ ID NO:15, A in SEQ ID NO:16, A in SEQ ID NO:17, G in SEQ ID NO:18, C in SEQ ID NO:19, T in SEQ ID NO:20, A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID NO:31, C in SEQ ID NO:32, C in SEQ ID NO:33, and/or C in SEQ ID NO:34 using the steps of:

(i) compute the linear combination of risk factors wi using the function $$w_i = \beta_{chol} * (cholesterol_i - 6) + \beta_{SPB} * (SBP_i - 120) + \beta_{smoker} * current_i + \sum_{j=1}^{J} \beta_{SNP_j} * (SNP_{i,j} - \overline{SNP_{i,j}})$$

wherein
  cholesterol: cholesterol level for the individual "i" in mmol/L.
  $\beta_{chol}$: logarithm of hazard ratio corresponding to the cholesterol (Table E).
  $SBP_i$: systolic blood pressure for the individual "i" in mmHg.
  $\beta_{SBP}$: logarithm of hazard ratio corresponding to systolic blood pressure (Table E).
  $current_i$: current smoking status for the individual "i" (1: current, 0: former/never).
  $\beta_{smoker}$: logarithm of hazard ratio corresponding to systolic blood pressure (Table E).

$$\sum_{j=1}^{J} \beta_{SNP_j} * (SNP_{i,j} - \overline{SNP_{i,j}})$$

a.

$$\sum_{j=1}^{J}$$

summary function along the J genetic variants.
  b. $\beta_{SNP_j}$ logarithm of hazard ratio corresponding to the genetic variant "j". The possible range of values of the β for each genetic variant "j" is shown in table B.
  c. $SNP_{j,i}$: number of risk alleles (0,1,2) for a specific genetic variant "j" included in the equation for an individual "i".
  d. $\overline{SNP_j}$: average risk allele number of copies for genetic variant "j" in the population, (ii) compute the baseline survival $S_0$ for a given age using the function $$S_0(age) = \exp\{-\exp(\alpha) * (age - 20)^p\}$$

$$S_0(age+10) = \exp\{-\exp(\alpha) * (age - 10)^p\}$$

wherein
  α, p: shape and scale parameters of the weibull distribution wherein their values are shown in Table F (parameters)
  exp: natural exponentiation, (iii) compute 10 years survival $S_{10}(age)$ using the function $$S(age) = \{S_0(age)\}^{\exp(w)}$$

$$S(age+10) = \{S_0(age+10)\}^{\exp(w)}$$

$$S_{10}(age) = S(age+10)/S(age)$$

(iv) compute the probability of having the event during the 10 years follow-up $Risk_{10}(age)$ using the function, $$Risk_{10}(age)=1-S_{10}(age)$$

and (v) compute the probability of having a cardiovascular event during the 10 years follow-up as the sum of coronary and non-coronary cardiovascular risk using the function $$CVDRisk_{10}=[CHDRisk_{10}(age)]+[Non\text{-}CHDRisk_{10}(age)]$$

8. A method as defined in any one of items 1 to 7 wherein the presence at position 27 is C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, G in SEQ ID NO:12, and A in SEQ ID NO:16.

9. A method as defined in any one of items 1 or 2 wherein the presence at position 27 is C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, G in SEQ ID NO:12, and A in SEQ ID NO:16.

10. A method as defined in any one of items 1 to 7 wherein the presence at position 27 is C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, and the A in SEQ ID NO:9, A in SEQ ID NO:10, G in SEQ ID NO:12, and A in SEQ ID NO:16, the latter four constituting haplotype B ALOX5AP 11. A method as defined in any one of items 1 to 7 wherein the presence at position 27 is C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, and A in SEQ ID NO:9, A in SEQ ID NO:10, A in SEQ ID NO:11 and G in SEQ ID NO:12, the latter four constituting haplotype B ALOX5 AP.

12. A method as defined in any one of items 1 to 7 wherein the presence at position 27 is C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, and G in SEQ ID NO:8.

13. A method as defined in any one of items 1 to 7 wherein the presence at position 27 is C in SEQ ID NO:2, T in SEQ ID NO:3, C in SEQ ID NO:5, and G in SEQ ID NO:8.

14. A method as defined in any one of items 1 to 7 wherein the presence at position 27 is T in SEQ NO:31, C in SEQ NO:32, C in SEQ NO:33, and C in SEQ NO:34.

15. A method as defined in any of the items 1 to 4 and 9 to 14 wherein the cardiovascular event is selected from the group of fatal or non-fatal myocardial infarction, stroke, angina pectoris, transient ischemic attacks, peripheral arterial disease or a combination thereof.

16. A method as defined in any of items 1 to 15 further comprising determining one or more cardiovascular disease or disorder risk factor(s) selected from the group consisting of age, race, sex, body mass index, blood pressure, smoking status, low density lipoprotein (LDL)- or high density lipoprotein (HDL)-cholesterol level, systolic blood pressure, diastolic blood pressure, history of heart failure, diabetes, renal insufficiency, left ventricular hypertrophy, alcohol consumption history, smoking history, exercise history, diet, and family history of cardiovascular disease or disorder.

17. The method according to any one of items 1 to 16 wherein the sample is an oral tissue sample, scraping, or wash or a biological fluid sample, preferably saliva, urine or blood.

18. The method according to any one or more of items 1 to 17 wherein the presence or absence of the polynucleotide is identified by amplifying or failing to amplify an amplification product from the sample, wherein the amplification product is preferably digested with a restriction enzyme before analysis and/or wherein the SNP is identified by hybridizing the nucleic acid sample with a primer label which is a detectable moiety.

19. A method as defined in items 5 to 18 wherein a plurality of classical risk factors "p" are used being said plurality being selected from the group of:
Sex, age, Total cholesterol, HDL-cholesterol, blood pressure, diabetes and smoking,
Age, LDL-cholesterol, HDL-cholesterol, triglycerides, systolic blood pressure, family story of myocardial infarction and diabetes,
Sex, Log(age/10), total cholesterol/HDL-cholesterol, body mass index, family story of premature CVD, smoking, Townsend score of output area, systolic blood pressure, treatment for hypertension and interaction $SBP^+HTN$ treatment.

20. A method as defined in items 5 to 18 wherein the probability is determined for the period from 35 to 75 years of age of the subject.

21. A method as defined in items 5 to 18 wherein the probability is determined for the period from the actual age of the subject and until the age of 75 years of age of the subject.

22. A computer program or a computer-readable media containing means for carrying out a method as defined in any of items 1 to 21.

23. A kit comprising reagents for detecting the identity of the nucleotide at position 27 within a nucleic acid sequence selected from the group of SEQ ID NO:1 to 34.

24. A kit as defined in item 23 which comprises one or more primer pairs specific for the amplification of a region comprising at least position 27 within a nucleic acid sequence of SEQ ID NO:1 to 34.

25. A kit as defined in item 23 or 24 where the sequences selected are SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, and SEQ ID NO:16.

26. A kit as defined in item 23 or 24 where the sequences selected are SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12.

27. A kit as defined in items 23 or 24 where the sequences selected are SEQ ID NO:1, SEQ ID NO:2, SEQ ID NO:3, SEQ ID NO:4, SEQ ID NO:5, SEQ ID NO:6, SEQ ID NO:7, SEQ ID NO:8, and sequences SEQ ID NO:9, SEQ ID NO:10, SEQ ID NO:12, and SEQ ID NO:16, the latter four constituting haplotype B ALOX5 AP.

28. A kit as defined in items 22 or 23 where the sequences selected are SEQ ID NO:1, SEQ ID NO:2, SEQ ID NO:3, SEQ ID NO:4, SEQ ID NO:5, SEQ ID NO:6, SEQ ID NO:7, SEQ ID NO:8, and the sequences SEQ ID NO:9, SEQ ID NO:10, SEQ ID NO:11, and SEQ ID NO:12, the latter four constituting haplotype B ALOX5 AP.

29. A kit as defined in items 23 or 24 where the sequences selected are SEQ ID NO:1, SEQ ID NO:2, SEQ ID NO:3, SEQ ID NO:4, SEQ ID NO:5, SEQ ID NO:6, SEQ ID NO:7, and SEQ ID NO:8.

30. A kit as defined in items 23 or 24 where the sequences selected are SEQ ID NO:2, SEQ ID NO:3, SEQ ID NO:5, and SEQ ID NO:8.

31. A kit as defined in items 21 or 24 or where the sequences selected are SEQ NO:31, SEQ NO:32, SEQ NO:33, and SEQ NO:34.

All values as obtained in the function(s) will be adapted to the regional or national prevalence, if necessary.

The terms "polymorphism" and "single nucleotide polymorphism" (i.e. SNP) are used herein interchangeably and relate to a nucleotide sequence variation occurring when a single nucleotide in the genome or another shared sequence differs between members of species or between paired chromosomes in an individual. A SNP can also be designated as a mutation with low allele frequency greater than about 1% in a defined population. Single nucleotide polymorphisms according to the present application may fall within coding sequences of genes, non-coding regions of genes or the intronic regions between genes.

The list of polymorphisms which are used in this method of the present invention is given in Table 1, included herewith as FIG. 2.

The term "cardiovascular disease or disorder", as used herein, includes diseases affecting the heart or blood vessels or both or associated with the cardiopulmonary and circulatory systems including—but not limited to—ischemia, angina pectoris, edematous conditions, artherosclerosis, Coronary Heart Disease, LDL oxidation, adhesion of monocytes to endothelial cells, foam-cell formation, fatty-streak development, platelet adherence, and aggregation, smooth muscle cell proliferation, reperfusion injury, high blood pressure, thrombotic disease, arrhythmia (atrial or ventricular or both); cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue, endotoxic, surgical, or traumatic shock; hypertension, valvular heart disease, heart failure, abnormal blood pressure; shock; vasoconstriction (including that associated with migraines); vascular abnormality, inflammation and/or insufficiency limited to a single organ or tissue.

In a preferred embodiment, the cardiovascular disease or cardiovascular event which risk is to be detected is selected from the group of fatal- and non-fatal myocardial infarction, stroke, angina pectoris, transient ischemic attacks, peripheral arteriopathy or a combination thereof.

The term "sample", as used herein, refers to any sample from a biological source and includes, without limitation, cell cultures or extracts thereof, biopsied material obtained from a mammal or extracts thereof, and blood, saliva, urine, feces, semen, tears, or other body fluids or extracts thereof.

When prediction models are used, as for instance, for making treatment decisions, predictive risks are categorized by using risk cutoff thresholds. The term "reclassification", as used herein, refers to the assignation of a person to another category of risk under a new model compared with the initial model of risk assessment. Reclassification is usually referred to as the percentage of persons being reclassified.

The term "Net Reclassification Improvement (NRI)" as used herein, refers to assessment of the net improvement in risk classification. NRI is calculated as the sum of differences in the proportion of individuals moving up minus the proportion moving down for cases and the proportion of individuals moving down minus the proportion moving up for non-cases. The components of NRI indicate the net benefit of reclassification improvement in cases and non-cases. Positive and negative values represent the net percentage of individuals with improved or worse classification, respectively. Overall, improvement in reclassification is indicated by an NRI significantly greater than 0.

The term "cardiovascular therapy", as used herein, refers to any type of treatment which results in the amelioration or reduces the risk of suffering any of the above mentioned cardiovascular diseases. Suitable therapies for use in the present invention include, without limitation, anticoagulants, antiplatelet agents, thrombolytic agents, antithrombotics, antiarrhythmic agents, agents that prolong repolarization, antihypertensive agents, vasodilator, antihypertensives, diuretics, inotropic agents, antianginal agents and the like.

Non-limiting examples of anticoagulants include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

Non-limiting examples of antiplatelet agents include aspirin, a dextran, dipyridamole (persantin), heparin, sulfinpyranone (anturane), clopidrogel and ticlopidine (ticlid). No limiting examples of thrombolytic agents include tissue plaminogen activator (activase), plasmin, pro-urokinase, urokinase (abbokinase) streptokinase (streptase), anistreplase/APSAC (eminase).

In certain embodiments wherein a patient is suffering from a hemorrhage or an increased likelihood of hemorrhaging, an agent that may enhance blood coagulation may be used. Non-limiting examples of a blood coagulation promoting agents include thrombolytic agent antagonists and anticoagulant antagonists. Non-limiting examples of anticoagulant antagonists include protamine and vitamine K1.

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, iamoparan, ozagrel, picotamide, plafibride, tedelparin, ticlopidine and triflusal.

Non-limiting examples of antiarrhythmic agents include Class I antiarrhythmic agents (sodium channel blockers), Class II antiarrhythmic agents (beta-adrenergic blockers), Class III antiarrhythmic agents (repolarization prolonging drugs), Class IV antiarrhythmic agents (calcium channel blockers) and miscellaneous antiarrhythmic agents.

Non-limiting examples of sodium channel blockers include Class IA, Class IB and Class IC antiarrhythmic agents. Non-limiting examples of Class IA antiarrhythmic agents include dispyramide (norpace), procainamide (pronestyl) and quinidine (quinidex). Non-limiting examples of Class IB antiarrhythmic agents include lidocaine (xylocaine), tocainide (tonocard) and mexiletine (mexitil). Non-limiting examples of Class IC antiarrhythmic agents include encainide (enkaid) and fiecainide (tambocor).

Non-limiting examples of beta blockers, otherwise known as beta-adrenergic blocker, a beta-adrenergic antagonists or Class II antiarrhythmic agents, include acebutolol (sectral), alprenolol, amosulalol, arotinolol, atenolol, befunolol, betaxolol, bevantolol, bisoprolol, bopindolol, bucumolol, bufetoiol, bufuralol, bunitrolol, bupranolol, butidrine hydrochloride, butofilolol, carazolol, carteolol, carvedilol, celiprolol, cetamolol, cloranolol, dilevalol, epanoiol, esmolol (brevibloc), indenolol, labetalol, levobunolol, mepindolol, metipranolol, metoprolol, moprolol, nadoiol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain embodiments, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

Non-limiting examples of agents with hypolipemic capabilities include, without limitation, bile acid sequestrants such as quaternary amines (e. g. cholestyramine and colestipol); nicotinic acid and its derivatives; HMG-CoA reductase inhibitors such as mevastatin, pravastatin, and simvastatin; gemfibrozil and other fibric acids, such as clofibrate, fenofibrate, benzafibrate and cipofibrate; probucol; raloxifene and its derivatives.

Non-limiting examples of agents that prolong repolarization, also known as Class III antiarrhythmic agents, include amiodarone (cordarone) and sotalol (betapace).

Non-limiting examples of calcium channel blocker, otherwise known as Class IV antiarrhythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinide derivative (e.g., cinnarizine, flunarizine, lidoflazine) or a micellaneous calcium channel blocker such as bencyclane, etafenone, magnesium, mibefradil or perhexiline. In certain embodiments a calcium channel blocker comprises a long-acting dihydropyridine (nifedipine-type) calcium antagonist.

Non-limiting examples of miscellaneous antiarrhythmic agents include adenosine (adenocard), digoxin (lanoxin), acecainide, ajmaline, amoproxan, aprindine, bretylium tosylate, bunaftine, butobendine, capobenic acid, cifenline, disopyranide, hydro quinidine, indecainide, ipatropium bromide, lidocaine, lorajmine, lorcainide, meobentine, moricizine, pirmenol, prajmaline, propafenone, pyrinoline, quinidine polygalacturonate, quinidine sulfate and viquidil.

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

Non-limiting examples of alpha blocker, also known as alpha-adrenergic blocker or an alpha-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an a blocker may comprise a quinazoline derivative. Non-limiting examples of quinazoline derivatives include alfuzosin, bunazosin, doxazosin, prazosin, terazosin and trimazosin. In certain embodiments, an antihypertensive agent is both an a and beta adrenergic antagonist. Non-limiting examples of an alpha/beta blocker comprise labetalol (normodyne, trandate).

Non-limiting examples of anti-angiotensin II agents include angiotensin converting enzyme inhibitors and angiotensin II receptor antagonists. Non-limiting examples of angiotensin converting enzyme inhibitors (ACE inhibitors) include alacepril, enalapril (vasotec), captopril, cilazapril, delapril, enalaprilat, fosinopril, lisinopril, moveitopril, perindopril, quinapril and ramipril. Non-limiting examples of angiotensin II receptor blocker, also known as angiotensin II receptor antagonist, ANG receptor blockers or an ANG-II type-1 receptor blockers (ARBS), include angiocandesartan, eprosartan, irbesartan, losartan and valsartan. Non-limiting examples of sympatholytics include centrally acting sympatholytics or peripherialiy acting sympatholytic. Non-limiting examples of centrally acting sympatholytics, also known as central nervous system (CNS) sympatholytics, include clonidine (catapres), guanabenz (wytensin) guanfacine (tenex) and methyldopa (aldomet). Non-limiting examples of a peripherally acting sympatholytic include ganglion blocking agents, an adrenergic neuron blocking agent, a beta-adrenergic blocking agent or a al-adrenergic blocking agent. Non-limiting examples of ganglion blocking agents include mecamylamine (inversine) and trimethaphan (arfonad). Non-limiting examples of adrenergic neuron blocking agents include guanethidine (ismelin) and reserpine (serpasil). Non-limiting examples of beta-adrenergic blockers include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha-adrenergic blockers include prazosin (minipress), doxazocin (cardura) and terazosin (hytrin).

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of coronary vasodilators include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(beta-diethylaminoethyl ether), hexobendine, itramin tosylate, khellin, lidoflanine, mannitol hexanitrane, medibazine, nicorglycerin, pentaerythritol tetranitrate, pentrinitrol, perhexiline, pimefylline, trapidil, tricramyl, trimetazidine, trolnitrate phosphate and visnadine.

In certain embodiments, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

Non-limiting examples of miscellaneous antihypertensives include ajmaline, gamma-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain embodiments, an antihypertensive may comprise an arylethanolamine derivative, a benzothiadiazine derivative, a 7V-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative. Non-limiting examples of arylethanolamine derivatives include amosulalol, bufuralol, dilevalol, labetalol, pronethalol, sotalol and sulfinalol. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide. Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril. Non-limiting examples of dihydropyridine derivatives include amlodipine, felodipine, isradipine, nicardipine, nifedipine, nilvadipine, nisoldipine and nitrendipine. Non-limiting examples of guanidine derivatives include bethanidine, debrisoquin, guanabenz, guanacline, guanadrel, guanazodine, guanethidine, guanfacine, guanochlor, guanoxabenz and guanoxan. Non-limiting examples of hydrazines/phthalazines include budralazine, cadralazine, dihydralazine, endralazine, hydracarbazine, hydralazine, pheniprazine, pildralazine and todraiazine. Non-limiting examples of imidazole derivatives include clonidine, lofexidine, phentolamine, tiamenidine and tolonidine. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate. Non-limiting examples of reserpine derivatives include bietaserpine, deserpidine, rescinnamine, reserpine and syrosingopine. Non-limiting examples of sulfonamide derivatives include ambuside, clopamide, furosemide, indapamide, quinethazone, tripamide and xipamide. Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine. Non-limiting examples of agents for the treatment of congestive heart failure include anti-angiotensin II agents, afterload-preload reduction treatment, diuretics and inotropic agents.

In certain embodiments, an animal, e.g. a human, patient that cannot tolerate an angiotensin antagonist may be treated with a combination therapy. Such therapy may combine adminstration of hydralazine (apresoline) and isosorbide dinitrate (isordil, sorbitrate).

Non-limiting examples of diuretics include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furterene, triamterene), purines (e.g., acefylline, 7-morpholinomethyl-theophyliine, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydrocarbazine, isosorbide, mannitol, metochalcone, muzolimine, perhexiline, ticrnafen and urea.

Non-limiting examples of positive inotropic agents, also known as cardiotonics, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, giycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular embodiments, an intropic agent is a cardiac glycoside, beta-adrenergic agonist or a phosphodiesterase inhibitor. Non-limiting examples of cardiac glycosides include digoxin (lanoxin) and digitoxin (crystodigin). Non-limiting examples of beta-adrenergic agonists include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethy norepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include amrinone (inocor).

Antianginal agents may comprise organonitrates, calcium channel blockers, beta blockers and combinations thereof. Non-limiting examples of organonitrates, also known as nitrovasodilators, include nitroglycerin (nitro-bid, nitrostat), isosorbide dinitrate (isordil, sorbitrate) and amyl nitrate (aspirol, vaporole). Endothelin (ET) is a 21-amino acid peptide that has potent physiologic and pathophysiologic effects that appear to be involved in the development of heart failure. The effects of ET are mediated through interaction with two classes of cell surface receptors. The type A receptor (ET-A) is associated with vasoconstriction and cell growth while the type B receptor (ET-B) is associated with endothelial-cell mediated vasodilation and with the release of other neurohormones, such as aldosterone. Pharmacologic agents that can inhibit either the production of ET or its ability to stimulate relevant cells are known in the art. Inhibiting the production of ET involves the use of agents that block an enzyme termed endothelin-converting enzyme that is involved in the processing of the active peptide from its precursor. Inhibiting the ability of ET to stimulate cells involves the use of agents that block the interaction of ET with its receptors. Non-limiting examples of endothelin receptor antagonists (ERA) include Bosentan, Enrasentan, Ambrisentan, Darusentan, Tezosentan, Atrasentan, Avosentan, Clazosentan, Edonentan, sitaxsentan, TBC 3711, BQ 123, and BQ 788.

Those skilled in the art will readily recognize that the analysis of the nucleotides present according to the method of the invention in an individual's nucleic acid can be done by any method or technique capable of determining nucleotides present in a polymorphic site. As it is obvious in the art, the nucleotides present in the polymorphic markers can be determined from either nucleic acid strand or from both strands.

Once a biological sample from a subject has been obtained (e.g., a bodily fluid, such as urine, saliva, plasma, serum, or a tissue sample, such as a buccal tissue sample or a buccal cell) detection of a sequence variation or allelic variant SNP is typically undertaken. Virtually any method known to the skilled artisan can be employed. Perhaps the most direct method is to actually determine the sequence of either genomic DNA or cDNA and compare these sequences to the known alleles SNPs of the gene. This can be a fairly expensive and time-consuming process. Nevertheless, this technology is quite common and is well known.

Any of a variety of methods that exist for detecting sequence variations may be used in the methods of the invention. The particular method used is not important in the estimation of cardiovascular risk or treatment selection.

Other possible commercially available methods exist for the high throughput SNP identification not using direct sequencing technologies. For example, Illumina's Veracode Technology, Taqman® SNP Genotyping Chemistry and KASPar SNP genotyping Chemistry.

A variation on the direct sequence determination method is the Gene Chip™ method available from Affymetrix. Alternatively, robust and less expensive ways of detecting DNA sequence variation are also commercially available. For example, Perkin Elmer adapted its TAQman Assay™ to detect sequence variation. Orchid BioSciences has a method called SNP-IT™ (SNP-Identification Technology) that uses primer extension with labeled nucleotide analogs to determine which nucleotide occurs at the position immediately 3' of an oligonucleotide probe, the extended base is then identified using direct fluorescence, an indirect colorimetric assay, mass spectrometry, or fluorescence polarization. Sequenom uses a hybridization capture technology plus MALDI-TOF (Matrix Assisted Laser Desorption/Ionization--Time-of-Flight mass spectrometry) to detect SNP genotypes with their MassARRAY™ system. Promega provides the READIT™ SNP/Genotyping System (U.S. Pat. No. 6,159,693). In this method, DNA or RNA probes are hybridized to target nucleic acid sequences. Probes that are complementary to the target sequence at each base are depolymerized with a proprietary mixture of enzymes, while probes which differ from the target at the interrogation position remain intact. The method uses pyrophosphorylation chemistry in combination with luciferase detection to provide a highly sensitive and adaptable SNP scoring system. Third Wave Technologies has the Invader OS™ method that uses proprietary Cleaveseq enzymes, which recognize and cut only the specific structure formed during the Invader process. Invader OS relies on linear amplification of the signal generated by the Invader process, rather than on exponential amplification of the target. The Invader OS assay does not utilize PCR in any part of the assay. In addition, there are a number of forensic DNA testing labs and many research labs that use gene-specific PCR, followed by restriction endonuclease digestion and gel electrophoresis (or other size separation technology) to detect restriction fragment length polymorphisms (RFLPs).

In various embodiments of any of the above aspects, the presence or absence of the SNPs is identified by amplifying or failing to amplify an amplification product from the sample. Polynucleotide amplifications are typically template-dependent. Such amplifications generally rely on the existence of a template strand to make additional copies of the template. Primers are short nucleic acids that are capable of priming the synthesis of a nascent nucleic acid in a template-dependent process, which hybridize to the template strand. Typically, primers are from ten to thirty base pairs in length, but longer sequences can be employed. Primers may be provided in double-stranded and/or single-stranded form, although the single-stranded form generally is preferred. Often, pairs of primers are designed to selectively hybridize to distinct regions of a template nucleic acid, and are contacted with the template DNA under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

Polymerase Chain Reaction

A number of template dependent processes are available to amplify the oligonucleotide sequences present in a given template sample. One of the best known amplification methods is the polymerase chain reaction. In PCR, pairs of primers that selectively hybridize to nucleic acids are used under conditions that permit selective hybridization. The term "primer", as used herein, encompasses any nucleic acid that is capable of priming the synthesis of a nascent nucleic acid in a template-dependent process. Primers may be provided in double-stranded or single-stranded form, although the single-stranded form is preferred. Primers are used in any one of a number of template dependent processes to amplify the target gene sequences present in a given template sample. One of the best known amplification methods is PCR.,which is described in detail in U.S. Pat. Nos. 4,683,195, 4,683,202 and 4,800,159, each incorporated herein by reference. In PCR, two primer sequences are prepared which are complementary to regions on opposite complementary strands of the target-gene(s) sequence. The primers will hybridize to form a nucleic-acid:primer complex if the target-gene(s) sequence is present in a sample. An excess of deoxyribonucleoside triphosphates is added to a reaction mixture along with a DNA polymerase, e.g. Taq polymerase, that facilitates template-dependent nucleic acid synthesis. If the target-gene(s) sequence:primer complex has been formed, the polymerase will cause the primers to be extended along the target-gene(s) sequence by adding on nucleotides. By raising and lowering the temperature of the reaction mixture, the extended primers will dissociate from the target-gene(s) to form reaction products, excess primers will bind to the target-gene(s) and to the reaction products and the process is repeated. These multiple rounds of amplification, referred to as "cycles", are conducted until a sufficient amount of amplification product is produced.

The amplification product may be digested with a restriction enzyme before analysis. In still other embodiments of any of the above aspects, the presence or absence of the SNP is identified by hybridizing the nucleic acid sample with a primer labeled with a detectable moiety. In other embodiments of any of the above aspects, the detectable moiety is detected in an enzymatic assay, radioassay, immunoassay, or by detecting fluorescence. In other embodiments of any of the above aspects, the primer is labeled with a detectable dye (e.g., SYBR Green I, YO-PRO-I, thiazole orange, Hex, pico green, edans, fluorescein, FAM, or TET). In other embodiments of any of the above aspects, the primers are located on a chip. In other embodiments of any of the above aspects, the primers for amplification are specific for said SNPs.

Another method for amplification is the ligase chain reaction ("LCR"). LCR differs from PCR because it amplifies the probe molecule rather than producing an amplicon through polymerization of nucleotides. In LCR, two complementary probe pairs are prepared, and in the presence of a target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750, incorporated herein by reference, describes a method similar to LCR for binding probe pairs to a target sequence.

Isothermal Amplification

An isothermal amplification method, in which restriction endonucleases and ligases are used to achieve the amplification of target molecules that contain nucleotide 5'-[[alpha]-thio]-triphosphates in one strand of a restriction site also may be useful in the amplification of nucleic acids in the present invention. In one embodiment, loop-mediated isothermal amplification (LAMP) method is used for single nucleotide polymorphism (SNP) typing.

Strand Displacement Amplification

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection.

Transcription-Based Amplification

Other nucleic acid amplification procedures include transcription-based amplification systems, including nucleic acid sequence based amplification. In nucleic acid sequence based amplification, the nucleic acids are prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer, which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

Other amplification methods may be used in accordance with the present invention. In one embodiment, "modified" primers are used in a PCR-like, template and enzyme dependent synthesis. The primers may be modified by labeling with a capture moiety (e.g., biotin) and/or a detector moiety (e.g., enzyme). In the presence of a target sequence, the probe binds and is cleaved catalytically. After cleavage, the target sequence is released intact to be bound by excess probe. Cleavage of the labeled probe signals the presence of the target sequence. In another approach, a nucleic acid amplification process involves cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Methods for Nucleic Acid Separation

It may be desirable to separate nucleic acid products from other materials, such as template and excess primer. In one embodiment, amplification products are separated by agarose, agarose-acrylamide or polyacrylamide gel electrophoresis using standard methods (Sambrook et al. 1989, see infra). Separated amplification products may be cut out and eluted from the gel for further manipulation. Using low melting point agarose gels, the separated band may be removed by heating the gel, followed by extraction of the nucleic acid. Separation of nucleic acids may also be effected by chromatographic techniques known in the art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC. In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to X-ray film or visualized with light exhibiting the appropriate excitatory spectra.

Alternatively, the presence of the polymorphic positions according to the methods of the invention can be determined by hybridisation or lack of hybridisation with a suitable nucleic acid probe specific for a polymorphic nucleic acid but not with the non-mutated nucleic acid. By "hybridize" is meant a pair to form a double-stranded molecule between complementary polynucleotide sequences, or portions thereof, under various conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 [mu]g/ml denatured salmon sperm DNA (ssDNA). In a most preferred embodiment, hybridization will occur at 42° C. in 250 mM NaCl, 25 mM trisodium citrate, 1% SDS, 50% formamide, and 200 [mu]g/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York, 1989.

Nucleic acid molecules useful for hybridisation in the methods of the invention include any nucleic acid molecule which exhibits substantial identity so as to be able to specifically hybridise with the target nucleic acids. Polynucleotides having "substantial identity" to an endogenous sequence are typically capable of hybridizing with at least one strand of a double-stranded nucleic acid molecule. By "substantially identical" is meant a polypeptide or nucleic acid molecule exhibiting at least 50% identity to a reference amino acid sequence or nucleic acid sequence. Preferably, such a sequence is at least 60%, more preferably 80% or 85%, and more preferably 90%, 95% or even 99% identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BEST-FIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e<"3> and e<"100> indicating a closely related sequence.

A detection system may be used to measure the absence, presence, and amount of hybridization for all of the distinct sequences simultaneously. Preferably, a scanner is used to determine the levels and patterns of fluorescence.

Method to Reclassify the Patients to A More Appropriate Risk Status.

Another object of the present invention is the improvement of the cardiovascular risk scales/methods/functions nowadays in use by introducing in the function the risk conferred by the particular combination of SNP markers as set out in table 1 associated with a risk of cardiovascular disease/disorder and/or with a risk of cardiovascular disease complications or event including, but not limited to, myocardial infarction, stroke, angina pectoris, transient ischemic attacks, congestive heart failure, aortic aneurysm and death. Cardiovascular risk factors nowadays in use include, but are not limited to, the original Framingham function, the adapted Framingham function (such as but not limited to REGICOR function), PROCAM function, SCORE function, and QRISK function. The improvement of the Framingham, PROCAM, REGICOR and QRISK functions is shown as functions 1a and 1b.

Function 1a (See Also Claim 5)

This general equation can be used to calculate the coronary or cardiovascular risk using the risk factors and effects of the risk factors included and defined in the Framingham (the original and/or the adapted such as but not limited to REGICOR), PROCAM and QRISK functions:

wherein, $$prob(event_i \mid CRF_{p,i}, SNP_{j,i}) = 1 - \hat{S}^{\exp\left[\frac{\sum_{p=1}^{P}\beta_{CRF_p}*CRF_{p,i} + \sum_{j=1}^{J}\beta_{SNP_j}*SNP_{j,i}-}{\sum_{p=1}^{P}\beta_{CRF_p}*\overline{CRF_p} - \sum_{j=1}^{J}\beta_{SNP_j}*\overline{SNP_j}}\right]}$$

prob(event|CRF,SNP): probability of presenting a coronary event given a combination of coronary risk factors (CRF) and genetic characteristics (SNP).

a. $event_i$: coronary event (fatal and non-fatal myocardial infarction or angina) in a 10-year period for an individual "i".

b. $CRF_{p,i}$: value of each coronary risk factor "p" included in the equation for an individual "i". The list of coronary risk factors included in the model is shown in table A.

c. $SNP_{j,i}$: number of risk alleles (0,1,2) for a specific genetic variant "j" included in the equation for an individual "i". The variants currently included in the model are shown in table B.

$\hat{S}$: mean survival free of coronary events at the population. This survival will be adapted to the regional or national rates.

exp: natural exponentiation.

$$\sum_{p=1}^{P} \beta_{CRF_p} * CRF_{p,i}:$$

where a.

$$\sum_{p=1}^{P}$$

summatory function along the P classical risk factors.

b. $\beta_{CRF_p}$ logarithm of hazard ratio corresponding to the classical coronary risk factor "p". The values of the β for each coronary risk factor "p" are shown in table C.

c. $CRF_{p,i}$: value of each coronary risk factor "p" included in the equation for an individual "i".

$$\sum_{j=1}^{J} \beta_{SNP_j} * SNP_{i,j}:$$

where a.

$$\sum_{j=1}^{J}$$

summatory function along the J genetic variants.

b. $\beta_{SNP_j}$ logarithm of hazard ratio corresponding to the genetic variant "j". The possible range of values of the β for each genetic variant "j" is shown in table B c. $SNP_{j,i}$: number of risk alleles (0,1,2) for a specific genetic variant "j" included in the equation for an individual "i".

$\overline{CRF_p}$: average value for the classical risk factor "p" in the population. This average value will be adapted to the regional or national prevalence.

$\overline{SNP_j}$: average risk allele number of copies for genetic variant "j" in the population. This average value will be adapted to the regional or national prevalence.

TABLE A

List of coronary risk factors included in the present inventive model, logarithm of hazard ratio, $\beta_{CRF_p}$, for every classical risk factor by gender, range of the average values for the classical risk factor "p" in the population, and mean survival free of coronary events rate at the population ($\hat{S}$) (range of possible values).

| | $CRF_p$ | $\beta_{CRF_p}$ for Men | $\beta_{CRF_p}$ for Women | $\overline{CRF_p}$ |
|---|---|---|---|---|
| FRAMINGHAM (original or adaptation) | Age | 0.048 | 0.338 | 35-74 |
| | $Age^2$ | 0 | −0.003 | |
| | Total cholesterol (mg/dL) | | | |
| | <160 | −0.659 | −0.261 | 0-30 |
| | 160-<200 | 0 | 0 | 0-30 |
| | 200-<240 | 0.177 | 0.208 | 0-30 |
| | 240-<280 | 0.505 | 0.244 | 0-30 |
| | ≥280 | 0.657 | 0.53 | 0-30 |
| | HDL Cholesterol (mg/dL) | | | |
| | <35 | 0.497 | 0.843 | 0-30 |
| | 35-<45 | 0.243 | 0.378 | 0-30 |
| | 45-<50 | 0 | 0.198 | 0-30 |
| | 50-<60 | −0.051 | 0 | 0-30 |
| | ≥60 | −0.487 | −0.430 | 0-30 |
| | Blood pressure | | | |
| | Optimal | −0.002 | −0.534 | 0-30 |
| | Normal | 0 | 0 | 0-30 |
| | Bordeline-High | 0.283 | −0.068 | 0-30 |
| | Hypertension I | 0.522 | 0.263 | 0-30 |
| | Hypertension II | 0.619 | 0.466 | 0-30 |
| | Diabetes | 0.428 | 0.597 | 0-30 |
| | Smoking | 0.523 | 0.292 | 0-60 |
| PROCAM | Age | 0.103 | — | 35-74 |
| | LDL-cholesterol (mg/dL) | 0.013 | — | 100-250 |
| | HDL-cholesterol (mg/dL) | −0.032 | — | 35-65 |
| | Triglycerides (mg/dL) | 0.317 | — | 100-200 |
| | Systolic blood pressure (mmHg) | 0.010 | — | 100-160 |
| | Family history of MI | 0.382 | — | 1-45 |
| | Diabetes | 0.399 | — | 0-30 |
| QRISK | Log(age/10) | 4.474 | 3.925 | 35-74 |
| | Total cholesterol/HDL chol. | 0.001 | 0.001 | 2-10 |
| | Body mass index (kg/m²) | 0.015 | 0.022 | 22-32 |
| | Family history of premature CVD | 0.206 | 0.262 | 1-45 |
| | Smoking | 0.425 | 0.349 | 0-60 |
| | Townsend score of output area | 0.034 | 0.017 | −3-3 |
| | Systolic blood pressure (mmHg) | 0.005 | 0.004 | 100-160 |
| | Treatment for hypertension | 0.550 | 0.614 | 0-40 |
| | Interaction SBP*HTN treatment | −0.004 | −0.007 | — |
| | Mean Survival $\hat{S}$ | 0.951 (0.01-9.00) | 0.978 (0.01-9.00) | |

TABLE B

Variants currently included in the present inventive model logarithm of hazard ratio (range of possible values), $\beta_{SNPj}$, and average risk allele number of copies (range of possible values), $\overline{SNP_j}$, for every genetic variant.

| $SNP_j$ | $\beta_{SNPj}$ | $\overline{SNP_j}$ |
|---|---|---|
| rs17465637 | 0.1310 (0.0100-0.5000) | 1.48 (0.3-2.8) |
| Rs67258887 | 0.1310 (0.0100-0.5000) | 0.3 (0.15-1.4) |
| Rs9818870 | 0.1133 (0.0100-0.5000) | 0.36 (0.15-1.4) |
| Rs12526453 | 0.0953 (0.0100-0.5000) | 1.34 (0.3-2.8) |
| Rs1333049 | 0.2546 (0.0100-1.0000) | 0.92 (0.3-2.8) |
| Rs1746048 | 0.0862 (0.0100-0.5000) | 1.74 (0.3-2.8) |
| Rs9982601 | 0.1655 (0.0100-0.5000) | 0.3 (0.15-1.4) |
| Rs10455872 | 0.2852 (0.0100-1.0000) | 0.14 (0.1-1.4) |
| Rs17216473* | 0.1310 (0.0100-0.5000) | 0.08 (0.05-0.5) |
| Rs10507391* | 0.1310 (0.0100-0.5000) | 0.08 (0.05-0.5) |
| Rs9315051 | 0.0000 (0.0100-0.5000) | 1 (0.3-2.8) |
| Rs17222842* | 0.1310 (0.0100-0.5000) | 0.08 (0.05-0.5) |
| Rs6922269 | 0.0000 (0.0100-0.5000) | 1 (0.3-2.8) |
| Rs17228212 | 0.1906 (0.0100-0.5000) | 0.6 (0.3-2.8) |
| Rs4769874 | 0.0000 (0.0100-0.5000) | 1 (0.3-2.8) |
| Rs9315050* | 0.1310 (0.0100-0.5000) | 0.08 (0.05-0.5) |
| Rs9551963 | 0.0000 (0.0100-0.5000) | 1 (0.3-2.8) |
| Rs17222814 | 0.0000 (0.0100-0.5000) | 1 (0.3-2.8) |
| Rs3798220 | 0.4121 (0.0100-1.0000) | 0.04 (0.05-0.5) |
| CD005 | 1.5000 (0.0100-3.0000) | 0.004 (0.001-0.01) |
| Rs17114036 | 0.1570 (0.0100-0.5000) | 1.82 (0.3-2.8) |
| Rs17609940 | 0.0677 (0.0100-0.5000) | 1.5 (0.3-2.8) |
| Rs12190287 | 0.0770 (0.0100-0.5000) | 1.24 (0.3-2.8) |
| Rs11556924 | 0.0862 (0.0100-0.5000) | 1.24 (0.3-2.8) |
| Rs4773144 | 0.0677 (0.0100-0.5000) | 0.88 (0.3-2.8) |
| Rs2895811 | 0.0677 (0.0100-0.5000) | 0.86 (0.3-2.8) |
| Rs3825807 | 0.0770 (0.0100-0.5000) | 1.14 (0.3-2.8) |
| Rs216172 | 0.0677 (0.0100-0.5000) | 0.74 (0.3-2.8) |
| Rs12936587 | 0.0677 (0.0100-0.5000) | 1.12 (0.3-2.8) |
| Rs46522 | 0.0583 (0.0100-0.5000) | 1.06 (0.3-2.8) |
| Rs974819 | 0.0677 (0.0100-0.5000) | 0.06 (0.01-0.5) |
| Rs4380028 | 0.0677 (0.0100-0.5000) | 1.2 (0.3-2.8) |
| Rs10953541 | 0.0677 (0.0100-0.5000) | 1.5 (0.3-2.8) |
| Rs2505083 | 0.0677 (0.0100-0.5000) | 0.84 (0.3-2.8) |

*All these SNPs define the ALOX5AP haplotype B that has an effect size defined by the β value 0.1310.

Function 1b (See Also Claim 6)

This general equation can be used to calculate the coronary or cardiovascular risk using the risk factors and effects of the risk factors included and defined in the Framingham (the original and/or the adapted such as but not limited to REGICOR), PROCAM and QRISK functions:

$$prob(event_i \mid CRF_{p,i}, GRS_i) = 1 - \hat{S}^{exp\left[\sum_{p=1}^{P} \beta_{CRF_p} * CRF_{p,i} + \beta_{GRS} * GRS_i - \sum_{p=1}^{P} \beta_{CRF_p} * \overline{CRF_p} - \beta_{GRS} * \overline{GRS}\right]}$$

wherein
prob(event$_i$|CRF$_{p,i}$,GRS$_i$): probability of presenting a coronary event given a combination of coronary risk factors (CRF) and genetic risk score (GRS).
  a. event$_i$: coronary event (fatal and non-fatal myocardial infarction or angina) in a 10-year period for an individual "i".
  b. CRF$_{p,i}$: value of each coronary risk factor "p" included in the equation for an individual "i". The list of coronary risk factors included in the model is shown in table C.
  c. GRS$_i$: genetic risk score defined as the weighted number of risk alleles (0,1,2) for the genetic variants included in the equation for an individual "i". The variants currently included in the genetic risk score are shown in table B. The weights are proportional to the betas of each SNP included in the score (shown in table B), and the range of the GRS goes from 0 to twice the number of SNPs included in the score.
$\hat{S}$: mean survival free of coronary events at the population. This survival will be adapted to the regional or national rates.
exp: natural exponentiation.

$$\sum_{p=1}^{P} \beta_{CRF_p} * CRF_{p,i}:$$

where
  a.

$$\sum_{p=1}^{P}$$

summatory function along the P classical risk factors.
  b. $\beta_{CRF_p}$ logarithm of hazard ratio corresponding to the classical coronary risk factor "p". The values of the β for each coronary risk factor "p" are shown in table C.
  c. CRF$_{p,i}$: value of each coronary risk factor "p" included in the equation for an individual "i".
$\beta_{GRS}$: logarithm of hazard ratio corresponding to one unit increase in the value of the genetic risk score. The value of this $\beta_{GRS}$ is 0.104 with a range of values going from 0.010 to 0.500.
$\overline{CRF_p}$: average value for the classical risk factor "p" in the population. This average value will be adapted to the regional or national prevalence.
$\overline{GRS}$: mean value of the genetic risk score in the population.

TABLE C

List of coronary risk factors included in the present inventive model, logarithm of hazard ratio, $\beta_{CRF_p}$, for every classical risk factor by gender, range of the average values for the classical risk factor "p" in the population, and mean survival free of coronary events rate at the population ($\hat{S}$) (range of possible values).

| | CRF$_P$ | $\beta_{CRF_p}$ for Men | $\beta_{CRF_p}$ for Women | $\overline{CRF_P}$ |
|---|---|---|---|---|
| FRAMINGHAM (original or adaptation) | Age | 0.048 | 0.338 | 35-74 |
| | Age$^2$ | 0 | −0.003 | |
| | Total cholesterol (mg/dL) | | | |
| | <160 | −0.659 | −0.261 | 0-30 |
| | 160-<200 | 0 | 0 | 0-30 |

TABLE C-continued

List of coronary risk factors included in the present inventive model, logarithm of hazard ratio, $\beta_{CRF_p}$, for every classical risk factor by gender, range of the average values for the classical risk factor "p" in the population, and mean survival free of coronary events rate at the population ($\hat{S}$) (range of possible values).

|   | $CRF_P$ | $\beta_{CRF_p}$ for Men | $\beta_{CRF_p}$ for Women | $\overline{CRF_P}$ |
|---|---|---|---|---|
|   | 200-<240 | 0.177 | 0.208 | 0-30 |
|   | 240-<280 | 0.505 | 0.244 | 0-30 |
|   | ≥280 | 0.657 | 0.53 | 0-30 |
|   | HDL Cholesterol (mg/dL) | | | |
|   | <35 | 0.497 | 0.843 | 0-30 |
|   | 35-<45 | 0.243 | 0.378 | 0-30 |
|   | 45-<50 | 0 | 0.198 | 0-30 |
|   | 50-<60 | −0.051 | 0 | 0-30 |
|   | ≥60 | −0.487 | −0.430 | 0-30 |
|   | Blood pressure | | | |
|   | Optimal | −0.002 | −0.534 | 0-30 |
|   | Normal | 0 | 0 | 0-30 |
|   | Bordeline-High | 0.283 | −0.068 | 0-30 |
|   | Hypertension I | 0.522 | 0.263 | 0-30 |
|   | Hypertension II | 0.619 | 0.466 | 0-30 |
|   | Diabetes | 0.428 | 0.597 | 0-30 |
|   | Smoking | 0.523 | 0.292 | 0-60 |
| PROCAM | Age | 0.103 | — | 35-74 |
|   | LDL-cholesterol (mg/dL) | 0.013 | — | 100-250 |
|   | HDL-cholesterol (mg/dL) | −0.032 | — | 35-65 |
|   | Triglycerides (mg/dL) | 0.317 | — | 100-200 |
|   | Systolic blood pressure (mmHg) | 0.010 | — | 100-160 |
|   | Family history of MI | 0.382 | — | 1-45 |
|   | Diabetes | 0.399 | — | 0-30 |
| QRISK | Log (age/10) | 4.474 | 3.925 | 35-74 |
|   | Total cholesterol/HDL chol. | 0.001 | 0.001 | 2-10 |
|   | Body mass index (kg/m$^2$) | 0.015 | 0.022 | 22-32 |
|   | Family history of premature CVD | 0.206 | 0.262 | 1-45 |
|   | Smoking | 0.425 | 0.349 | 0-60 |
|   | Townsend score of output area | 0.034 | 0.017 | −3-3 |
|   | Systolic blood pressure (mmHg) | 0.005 | 0.004 | 100-160 |
|   | Treatment for hypertension | 0.550 | 0.614 | 0-40 |
|   | Interaction SBP*HTN treatment | −0.004 | −0.007 | — |
|   | Mean Survival $\hat{S}$ | 0.951 (0.01-9.00) | 0.978 (0.01-9.00) | |

Function 1c (See Also Claim 7)

The cardiovascular risk will be calculated using the following equations using the SCORE risk function:

First step: compute linear combination of risk factors $$w_i = \beta_{chol} * (cholesterol_i - 6) + \beta_{SPB} * (SBP_i - 120) + \beta_{smoker} * current_i + \sum_{j=1}^{J} \beta_{SNP_j} * (SNP_{i,j} - \overline{SNP_{i,j}})$$

where $cholesterol_i$: cholesterol level for the individual "i" in mmol/L.

$\beta_{chol}$: logarithm of hazard ratio corresponding to the cholesterol (Table E).

$SBP_i$: systolic blood pressure for the individual "i" in mmHg.

$\beta_{SBP}$: logarithm of hazard ratio corresponding to systolic blood pressure (Table E).

$current_i$: current smoking status for the individual "i" (1: current, 0: former/never).

$\beta_{smoker}$: logarithm of hazard ratio corresponding to systolic blood pressure (Table E).

$$\sum_{j=1}^{J} \beta_{SNP_j} * (SNP_{i,j} - \overline{SNP_{i,j}}):$$

a.

$$\sum_{j=1}^{J}$$

summatory function along the J genetic variants.

b. $\beta_{SNP_j}$: logarithm of hazard ratio corresponding to the genetic variant "j". The possible range of values of the β for each genetic variant "j" is shown in table B.

c. $SNP_{j,i}$: number of risk alleles (0,1,2) for a specific genetic variant "j" included in the equation for an individual "i".

d. $\overline{SNP_j}$: average risk allele number of copies for genetic variant "j" in the population. This average value will be adapted to the regional or national prevalence.

Second step: compute baseline survival.

$$S_0(age)=\exp\{-\exp(\alpha)*(age-20)^p\}$$

$$S_0(age+10)=\exp\{-\exp(\alpha)*(age-10)^p\}$$

where

α, p: shape and scale parameters of the weibull distribution. Their values are shown in Table F (parameters)

exp: natural exponentiation

Third step: compute 10 years survival $$S(age)=\{S_0(age)\}^{exp(w)}$$

$$S(age+10)=\{S_0(age+10)\}^{exp(w)}$$

$$S_{10}(age)=S(age+10)/S(age)$$

Fourth step: compute probability of having the event during the 10 years follow-up.

$$Risk_{10}(age)=1-S_{10}(age)$$

Fifth step: compute the probability of having a cardiovascular event during the 10 years follow-up as the sum of coronary and non-coronary cardiovascular risk.

$$CVDRisk_{10}=[CHDRisk_{10}(age)]+[Non\text{-}CHDRisk_{10}(age)]$$

TABLE E

|  | CHD | Non-CHD CVD |
|---|---|---|
| Current smoker, $\beta_{smoker}$ | 0.71 | 0.63 |
| Cholesterol (mmol/L), $\beta_{chol}$ | 0.24 | 0.02 |
| Systolic blood pressure (mmHg), $\beta_{SBP}$ | 0.018 | 0.022 |

CHD: coronary heart disease
CVD: cardiovascular disease

TABLE F

| Country | | CHD | | Non-CHD CVD | |
|---|---|---|---|---|---|
| | | A | p | A | p |
| Low risk | Men | −22.1 | 4.71 | −26.7 | 5.84 |
| | Women | −29.8 | 6.36 | −31.0 | 6.62 |
| High risk | Men | −21.0 | 4.62 | −25.7 | 5.47 |
| | Women | −28.7 | 6.23 | −30.0 | 6.42 |

CHD: coronary heart disease
CVD: cardiovascular disease

Function 1d

The cardiovascular risk will be calculated using the following equations using the SCORE risk function:

First step: compute linear combination of risk factors $$w_i = \beta_{chol}*(cholesterol_i-6)+\beta_{SPB}*(SBP_i-120)+\beta_{smoker}*current_i+\beta_{GRS}*(GRS_i-\overline{GRS})$$

where $cholesterol_i$: cholesterol level for the individual "i" in mmol/L.

$\beta_{chol}$: logarithm of hazard ratio corresponding to the cholesterol (Table E).

$SBP_i$: systolic blood pressure for the individual "i" in mmHg.

$\beta_{SBP}$: logarithm of hazard ratio corresponding to systolic blood pressure (Table E).

$current_i$: current smoking status for the individual "i" (1: current, 0: former/never).

$\beta_{smoker}$: logarithm of hazard ratio corresponding to systolic blood pressure (Table E).

$\beta_{GRS}$: logarithm of Hazard ratio corresponding to one unit increase in the value of the genetic risk score. The value of this $\beta_{GRS}$ is 0.104 with a range of values going from 0.010 to 0.500.

$GRS_i$: genetic risk score for the individual "i" defined as the weighted number of risk alleles (0,1,2) for the genetic variants included in the equation for an individual "i". The variants currently included in the genetic risk score are shown in table B. The weights are proportional to the betas of each SNP included in the score (shown in table B), and the range of the GRS goes from 0 to twice the number of SNPs included in the score.

$\overline{GRS}$: mean value of the genetic risk score in the population.

Second step: compute baseline survival.

$$S_0(age)=\exp\{-\exp(\alpha)*(age-20)^p\}$$

$$S_0(age+10)=\exp\{-\exp(\alpha)*(age-10)^p\}$$

where

α, p: shape and scale parameters of the weibull distribution. Their values are shown in Table F (parameters)

exp: natural exponentiation

Third step: compute 10 years survival $$S(age)=\{S_0(age)\}^{exp(w)}$$

$$S(age+10)=\{S_0(age+10)\}^{exp(w)}$$

$$S_{10}(age)=S(age+10)/S(age)$$

Fourth step: compute probability of having the event during the 10 years follow-up $$Risk_{10}(age)=1-S_{10}(age)$$

Fifth step: compute the probability of having a cardiovascular event during the 10 years follow-up as the sum of coronary and non-coronary cardiovascular risk.

$$CVDRisk_{10}=[CHDRisk_{10}(age)]+[Non\text{-}CHDRisk_{10}(age)]$$

Surprisingly, the combination of SNP markers included in the present invention and set forth in table 1 and those combinations included in the different embodiments and using the functions described in functions 1a to 1d above have proved to be capable to reclassify the subjects classified as having moderate risk to suffer cardiovascular disease and/or cardiovascular events and/or cardiovascular complications with a higher accuracy than that obtained using the classical risk factors alone and using the scales/functions nowadays in use or published functions including genetic information.

Surprisingly, the combination of SNP markers included in the present invention and set forth in table 1 (FIG. 2) and those combinations included in the different embodiments and using the functions described in functions 1a to 1d above have proved to be capable to estimate in a precise manner the risk for a subject to suffer cardiovascular disease and/or cardiovascular events and/or cardiovascular complications with a higher accuracy than that obtained using the classical risk factors alone and using the functions nowadays in use or published functions including genetic information.

Surprisingly, the combination of SNP markers included in the present invention and set forth in table 1 (FIG. 2) and those combinations included in the different embodiments and using the functions described in functions 1a to 1d above have proved to obtain a higher validity and a superior validation in predicting cardiovascular disease and/or cardiovascular events and/or cardiovascular disease complications than that obtained using the classical risk factors alone and using the functions nowadays in use or published functions including genetic information. Moreover, the reclassification was also improved.

By the use of the functions described, a personalized risk is obtained for the development of coronary heart disease and/or cardiovascular events and/or cardiovascular disease, in particular fatal- and non-fatal-myocardium infarction, angina, stroke, transient ischemic attack, peripheral arteriopathy or a combination thereof. In accordance to the function used FRAMINGHAM (original or adapted), PROCAM study, QRISK and SCORE the risk will define to which risk stratum the subjects belong to. The method provided will upgrade (reclassify) those subjects wrongly classified with the methods used nowadays to calculate the cardiovascular risk to a more accurate risk stratum. As the treatment (preventive and/or therapeutic) is adapted to the level of risk, the reclassification will imply the use in a more effective manner the preventive and/or therapeutic measures that will decrease the incidence and/or recurrence of cardiovascular disease and cardiovascular disease complications such as—but not limited to—fatal- and non-fatal-myocardium infarction, angina, stroke, transient ischemic attack, peripheral arteriopathy or a combination thereof.

Example 1

One prospective population-based cohort was included: the REGICOR (Registre Gironi del Cor) cohort originally included 4,782 individuals from two population-based cross-sectional studies conducted in the province of Gerona, in north-eastern Spain, in 1995 and 2000 (Grau M, et al. Eur J Cardiovasc Prev Rehabil. 2007;14:653-659.) This is a population with low myocardial infarction incidence and low CHD mortality (Masia R, et al. J Epidemiol Community Health. 1998; 52:707-715). Participants aged 35 to 74 years who were free of CVD and had DNA and complete follow-up information available were selected for the present study. This study was approved by the local Ethics Committee and all participants gave written informed consent. All subjects were of European ancestry.

Genetic Variant Selection, Genotyping and Multi-Locus Risk Score Generation

We selected 9 genetic variants, associated with CHD but not with classical risk factors, to generate a multi-locus GRS as previously described (Lluis-Ganella C, et al. Rev Esp Cardiol. 2010;63:925-933). Genetic variants were mainly selected from the GWAS catalogue of the National Human Genome Research Institute (Hindorff L A, et al. Available at: www.genome.gov/26525384) and were associated with CHD but not with cardiovascular risk factors according to the data from this catalogue. The variants selected were: rs17465637 in MIA3 (Samani N J, et al. N Engl J Med. 2007; 357:443-453, Myocardial Infarction Genetics Consortium. Nat Genet. 2009; 41:334-341); rs6725887 in WDR12 (Myocardial Infarction Genetics Consortium. Nat Genet. 2009: 41:334-341); rs9818870 in MRAS (Erdmann J, et al. Nat Genet. 2009; 41:280-282); rs12526453 in PHACTR1 (Myocardial Infarction Genetics Consortium. Nat Genet. 2009;41:334-341); rs1333049 near CDKN2A/2B (Samani N J, et al. N Engl J Med. 2007:357:443-453, Myocardial Infarction Genetics Consortium. Nat Genet. 2009; 41:334-341, Helgadottir A, et al. Science. 2007; 316:1491-1493, McPherson R, et al. Science. 2007;316:1488-1491; rs1746048 near CXCL12 (Samani N J, et al. N Engl J Med. 2007;357:443-453, Myocardial Infarction Genetics Consortium. Nat Genet. 2009; 41:334-341); rs9982601 near SCL5A3 (Myocardial Infarction Genetics Consortium. Nat Genet. 2009; 41:334-341); rs10455872 in LPA (Shiftman D, et al. Atherosclerosis. 2010; 212:193-196); and the HaploB (rs10507391, rs9315051, rs17216473, rs17222842) in ALOX5AP (hapB) (Helgadottir A, et al. Nat Genet. 2004; 36:233-239).

A multi-locus GRS for each individual was constructed by summing the number of risk alleles (or risk haplotype) for each of the genetic variants. This GRS was weighted by the estimated effect size reported for each variant in the CARDIoGRAM study (CARDIoGRAM Consortium. Circ Cardiovasc Genet. 2010; 3:475-483).

REGICOR participants' DNA was obtained from buffy coat using standardized methods (L'ARS services, Barcelona, Spain) and samples were genotyped using the Cardio inCode chip (Ferrer inCode, Barcelona, Spain) based on Veracode and KASPar technologies by Centro Nacional de Investigation Oncolóogica (CNIO, Madrid, Spain). The overall percentage of agreement of the chip with reference technology is 99.9% and the analytical sensitivity and specificity is greater than 98.6%. Genotypic information for the Framingham participants was also obtained via dbGaP for genotyped (Affymetrix 500K and 50K chips) and imputed variants (HapMap CEU release 22, build 36, imputed using MACH version 1.00.15). Individuals with low call rates or sex mismatches were excluded before imputation in this database. Moreover, high levels of missingness ($p<10^{-9}$), highly significant departures from Hardy-Weinberg equilibrium ($p<10^{-6}$), or Mendelian errors (>100) were used to determine which SNPs to include in the imputation step, and were also applied as a quality control criteria for the SNPs selected.

Follow-Up and Phenotype Definition

All REGICOR participants were periodically contacted by telephone or by mail to ascertain whether they had presented any cardiovascular event up until the end of 2007. Fatal events were identified from regional and national mortality registers. All the reported events were reviewed with hospital records or primary care records. An event committee classified the suspected CVD events after review of all medical records and physician notes using standardized criteria (Grau M, et al. Prev Med. 2010; 51:78-84).

In these analyses we considered two groups of events: a) CHD events included myocardial infarction, angina, coronary revascularization and death due to CHD; and, b) cardiovascular events included CHD events, plus atherothrombotic stroke and peripheral artery disease.

Myocardial infarction was defined on the basis of the classical WHO definition by the presence of 2 out of 3 clinical criteria: new diagnostic Q-waves on ECG, prolonged ischemic chest discomfort and elevation of serum biomarkers of myocardial necrosis. Angina was defined by the presence of ischemic chest discomfort with signs of ischemia in the ECG. Coronary artery by-pass grafting or percutaneous coronary interventions were considered as revascularization procedures. CHD death was considered after reviewing the mortality register when the most likely cause of death was CHD and no other cause could be ascribed.

Atherothrombotic stroke was defined as a non-embolic acute-onset focal neurological deficit of vascular origin that persisted for more than 24 hours or an ischemic infarction that was documented at autopsy. Peripheral artery disease was defined by the presence of symptoms of claudication and an objective diagnostic test such as a pathological ankle-brachial index (<0.9) or a pathological arteriography or revascularization procedure.

Ten-Year Cardiovascular Risk Estimation

The risk function used in this study was the validated and calibrated REGICOR adaptation of the Framingham function to the risk factor prevalence and coronary event incidence of the Spanish population (Marrugat J, et al. J Epidemiol Community Health. 2003;57(8):634-638).

All cardiovascular risk factors required for the risk functions were measured using standard methods. Participants were considered to be diabetic if they had been diagnosed with diabetes or treated with oral hypoglycemic agents or insulin or presented a glycemia higher or equal to 126 mg/dL. Those who reported smoking ≥1 cigarette/day in the preceding year were considered smokers. All necessary baseline lipid and blood pressure measurements were collected and used to estimate the risk of each participant.

Statistical Analysis

We used classical parametric and non-parametric methods to compare the characteristics of different groups of individuals according to the presence of a CDV/CHD event during follow-up and within the different quintiles of the genetic risk score (GRS).

The association between the individual genetic variants or the multi-locus GRS and incidence of cardiovascular or coronary events was tested using Cox proportional hazards models; the GRS was considered as a continuous variable or was categorized according to its quintiles. All models were adjusted by the sum of the product of each classical risk factor and its coefficient estimated in the REGICOR risk functions calculated in each individual. The proportional hazards assumption was tested using the cox.zph function from the R package survival.

We used two different statistics to assess the potential value of including the GRS in risk prediction:
a) to assess the goodness-of-fit of the models we used a version of the Hosmer-Lemeshow test that takes right censoring of the data into account (D Agostino R B, Nam B H. Handbook of Statistics. 2003; Vol 23:1-25);
b) to assess the reclassification we calculated the net reclassification improvement (NRI) (Pencina M J, et al. Stat Med. 2011;30:11-21) in the whole sample and in the subgroup of individuals considered to have intermediate coronary risk according to the classical risk function. We defined three risk categories (low, intermediate and high) 0-4.9%, 5.0-14.9%, ≥15%, respectively. To calculate the 10-year expected number of events in each risk category, we used the Kaplan-Meier estimates as proposed by Steyerberg and Pencina (Steyerberg E W, Pencina M J. Ann Intern Med. 2010; 152(3):195-196). A bootstrapping method was used to construct confidence intervals for NRI to take into account the uncertainty of the Kaplan-Meier estimates.

All analyses were performed using R statistical package (version 2.11.1).

Results

Description of the Populations Studied

The number of participants included was 2,760 from the REGICOR cohort. The characteristics of the participants in the cohort, and by presence of CVD/CHD events are shown in Table G (FIG. 3).

The hazard ratio of CVD/CHD event is presented for each cardiovascular risk factor in table H. As expected, all classical risk factors, except smoking and family history of CHD, were associated with an increased risk of CVD and CHD events in the REGICOR cohort.

TABLE H

Hazard Ratio of classical risk factors for cardiovascular and for coronary events.

| REGICOR | CARDIOVASCULAR event | | CORONARY event | |
|---|---|---|---|---|
| | HR [95% CI] | p-value | HR [95% CI] | p-value |
| Age (10 years) | 1.94 [1.62-2.32] | <0.001 | 1.98 [1.60-2.45] | <0.001 |
| Gender (men) | 1.85 [1.28-2.63] | <0.001 | 1.89 [1.22-2.86] | 0.002 |
| Total cholesterol (10 mg/dL) | 1.06 [1.02-1.10] | 0.005 | 1.05 [1.01-1.10] | 0.027 |
| HDL cholesterol (10 mg/dL) | 0.63 [0.54-0.74] | <0.001 | 0.57 [0.47-0.69] | <0.001 |
| Systolic BP (10 mmHg) | 1.35 [1.25-1.45] | <0.001 | 1.37 [1.25-1.50] | <0.001 |
| Diastolic BP (10 mmHg) | 1.32 [1.13-1.55] | 0.001 | 1.39 [1.16-1.69] | 0.001 |
| Diabetes | 2.11 [1.41-3.14] | <0.001 | 2.70 [1.72-4.23] | <0.001 |
| Smoker | 1.10 [0.73-1.65] | 0.638 | 1.23 [0.77-1.97] | 0.383 |

TABLE H-continued

Hazard Ratio of classical risk factors for cardiovascular and for coronary events.

|  | CARDIOVASCULAR event | | CORONARY event | |
|---|---|---|---|---|
| REGICOR | HR [95% CI] | p-value | HR [95% CI] | p-value |
| Family history of CVD* | 1.35 [0.86-2.14] | 0.191 | 1.47 [0.86-2.49] | 0.160 |
| Coronary risk† | 1.13 [1.11-1.16] | <0.001 | 1.14 [1.12-1.17] | <0.001 |

*CVD: Cardiovascular disease.
†Corollary was calculated using the Framingham calibrated function for the REGICOR cohort.

The characteristics of the participants within each quintile of the GRS are shown in Table I. The score was not associated with any of the classical risk factors included in the Framingham calibrated risk function, except for family history of CHD.

TABLE I

Description of the characteristics of the participants across genetic risk score quintiles.

| | | Quintiles of genetic score | | | | | | |
|---|---|---|---|---|---|---|---|---|
| | Variables | Q1 | Q2 | Q3 | Q4 | Q5 | p-value | p-trend |
| REGICOR | N | 552 | 544 | 562 | 582 | 510 | | |
| | Age (years)* | 54.0 (11.2) | 53.2 (11.0) | 54.2 (11.1) | 54.1 (11.3) | 53.9 (11.1) | 0.550 | 0.645 |
| | Gender (men)† | 266 (48.2) | 269 (48.6) | 252 (44.8) | 285 (49.0) | 255 (50.0) | 0.463 | 0.521 |
| | Total cholesterol (mg/dL)* | 222 (44.1) | 227 (42.1) | 227 (41.8) | 230 (43.2) | 224 (42.0) | 0.018 | 0.189 |
| | HDL cholesterol (mg/dL)* | 51 (12.5) | 52 (13.1) | 53 (14.3) | 51 (12.9) | 51 (13.5) | 0.031 | 0.633 |
| | SBP (mmHg)* | 133 (22.0) | 131 (20.0) | 133 (20.2) | 133 (22.0) | 132 (19.4) | 0.539 | 0.696 |
| | DBP (mmHg)* | 79 (10.4) | 79 (10.8) | 79 (10.0) | 80 (10.4) | 80 (10.0) | 0.581 | 0.101 |
| | Diabetes† | 70 (13.0) | 79 (14.6) | 90 (16.4) | 83 (14.6) | 62 (12.4) | 0.357 | 0.831 |
| | Smoking† | 115 (21.2) | 121 (21.9) | 124 (22.2) | 135 (23.5) | 121 (24.2) | 0.775 | 0.124 |
| | Family history of CHD† | 45 (8.2) | 61 (11.2) | 76 (13.5) | 74 (12.8) | 68 (13.5) | 0.033 | 0.001 |
| | Coronary risk‡ | 3.4 (1.8-6.5) | 3.2 (1.6-5.7) | 3.6 (1.7-6.5) | 3.5 (1.8-6.6) | 3.4 (1.9-6.1) | 0.427 | 0.312 |
| | Cardiovascular events incidence§ | 6.41 | 8.12 | 5.16 | 8.46 | 7.90 | 0.068 | 0.027 |
| | Coronary events incidence§ | 4.38 | 5.69 | 3.34 | 6.20 | 7.52 | 0.088 | 0.034 |

HDL: high density lipoprotein; SBP: systolic blood pressure; DBP: diastolic blood pressure; CHD: coronary heart disease.
*mean (standard deviation); †n (proportion, %); ‡mean (95% confidence interval); §number of cases/100 individuals in 10 years.

The GRS adjusted for coronary risk showed a statistically significant association with CHD and CVD incidence when considered as a continuous variable (Table J). We observed a linear association with an increase of CVD and CHD events of 12% (95% CI 1%;24%) and 15% (95% CI: 2%;30%) per unit of the GRS, respectively (Table J). This association remained statistically significant with further adjustment for family history of CHD. Participants in the top quintile of GRS had 1.71 times and 1.81 times increased risk of CVD and CHD respectively, compared to the bottom quintile (p value for linear trend <0.025 and 0.039) (Table J).

TABLE J

Multivariate adjusted association of the genetic risk score with cardiovascular and coronary events as a linear variable and across quintiles.

| | | REGICOR | |
|---|---|---|---|
| Genetic risk score | | HR [95% CI]* | P-value |
| Cardiovascular events | Linear | 1.12 [1.01-1.24] | 0.038 |
| | Quintiles P-trend | | 0.025 |
| | Q1 | 1 | — |
| | Q2 | 1.26 [0.69-2.30] | 0.450 |
| | Q3 | 0.84 [0.44-1.57] | 0.575 |
| | Q4 | 1.59 [0.92-2.78] | 0.099 |
| | Q5 | 1.71 [0.97-3.031] | 0.066 |
| Coronary events | Linear | 1.15 [1.02-1.30] | 0.027 |
| | Quintiles P-trend | | 0.039 |
| | Q1 | 1 | — |

TABLE J-continued

Multivariate adjusted association of the genetic risk score with cardiovascular and coronary events as a linear variable and across quintiles.

| | REGICOR | |
|---|---|---|
| Genetic risk score | HR [95% CI]* | P-value |
| Q2 | 1.11 [0.54-2.28] | 0.774 |
| Q3 | 0.72 [0.34-1.54] | 0.398 |
| Q4 | 1.45 [0.76-2.79] | 0.263 |
| Q5 | 1.81 [0.94-3.48] | 0.074 |

All models were adjusted by the sum of the product of each classical risk factor and its coefficient estimated in the Framingham calibrated Regicor risk function.
* HR [95% CI]: Hazard ratio [95% confidence interval].

In FIG. 1 we present the distribution of genetic risk score in REGICOR participants according to the incidence of cardiovascular (a) and coronary (b) events during the follow-up. The genetic risk score is represented in the ordinal axis (X axis) and is computed as a cumulative sum of all the risk alleles that a person carries, weighted by the effect of each SNP, and theoretically ranging from 0 to 18 copies.

The goodness-of-fit test for the models for CHD by the Hosmer-Lemeshow test indicated that the calibration was good in the REGICOR cohort with and without the GRS ($\chi^2$=4.39; p-value=0.222 and $\chi^2$=5.58; p-value=0.232, respectively).

Risk Prediction Improvement Analyses

Table K shows the risk reclassification achieved with the GRS inclusion in the Framingham risk function for CVD and CHD events. When we considered the intermediate risk subgroup the NRI increased in both cohorts and for both outcomes. In the meta-analysis, the NRI were 10.32 [95% CI: 2.48;18.17] and 14.36 [95% CI: 5.14;24.12] for CVD and CHD events for the intermediate risk group, respectively. The results of a GRS with the 4 more informative SNPs (rs6725887, rs9818870, rs1333049, and LPA haplotype [rs3798220 and rs10455872]) were similar and are described in Table L.

TABLE L

Reclassification of individuals based on the 10-year predicted risk of coronary heart disease with and without the genetic risk score. Risk categories were defined using national recommendations. In REGICOR the cut-off points for low. Intermediate and high risk were 0-4.9%, 5-9.99% , 10-14.99% and ≥15%.

| | Plus genetic score | | | | | | | |
|---|---|---|---|---|---|---|---|---|
| | Coronary | | | | Vascular | | | |
| Only classical | <=0.05 | (0.05, 0.10] | (0.10, 0.15] | >0.15 | <=0.05 | (0.05, 0.10] | (0.10, 0.15] | >0.15 |
| Cases | | | | | | | | |
| (-Inf, 0.05] | 43.3 | 6.7 | 0.0 | 0.0 | 61.0 | 9.3 | 0.0 | 0.0 |
| (0.05, 0.10] | 1.4 | 38.4 | 8.1 | 0.0 | 0.4 | 52.7 | 30.4. | 0.0 |
| (0.10, 0.15] | 0.0 | 3.6 | 18.3 | 5.8 | 0.0 | 5.7 | 21.4 | 5.3 |
| (0.15, Inf] | 0.0 | 0.0 | 0.0 | 16.3 | 0.0 | 0.0 | 5.5 | 19.7 |
| Controls | | | | | | | | |
| (-Inf, 0.05] | 1695.0 | 89.3 | 0.0 | 0.0 | 1698.1 | 64.9 | 0.0 | 0.0 |
| (0.05, 0.10] | 92.3 | 468.0 | 55.8 | 1.0 | 77.3 | 484.3 | 39.8 | 0.0 |
| (0.10, 0.15] | 0.0 | 342 | 103.7 | 20.7 | 0.0 | 26.6 | 113.0 | 15.3 |
| (0.15, Inf] | 0.0 | 0.0 | 27.6 | 59.5 | 0.0 | 0.0 | 19.5 | 58.6 |
| NRI | Coronary | | | | Vascular | | | |
| ALL | 9.95 [1.02;18.89] | | | | 18.22 [3.71, 32.72] | | | |
| Moderate risk (10-20%) | 7.10 [−1.98;16.18] | | | | 16:37 [3. 17, 29.67] | | | |

TABLE K

Reclassification of individuals based on the 10-year predicted risk of coronary heart disease with and without the genetic risk score. Risk categories were defined using national recommendations. In REGICOR the cut-off points for low, intermediate and high risk were 0-4.9%, 5-14.9% and ≥15%.

| | REGICOR Classical function + Genetic Risk Score | | |
|---|---|---|---|
| Classical function | Low risk | Intermediate risk | High risk |
| Cardiovascular events | | | |
| Cases | | | |
| Low risk | 64 | 6 | 0 |
| Intermediate risk | 1 | 89 | 5 |
| High risk | 0 | 4 | 22 |
| Non-cases | | | |
| Low risk | 1669 | 77 | 0 |
| Intermediate risk | 77 | 648 | 22 |
| high risk | 0 | 19 | 57 |
| Coronary events | | | |
| Cases | | | |
| Low risk | 43 | 6 | 0 |
| Intermediate risk | 1 | 68 | 6 |
| High risk | 0 | 0 | 16 |
| Non-cases | | | |
| Low risk | 1671 | 96 | 0 |
| Intermediate risk | 92 | 642 | 33 |
| High risk | 0 | 25 | 61 |
| NRI | | | |
| Intermediate risk | | | |
| Cardiovascular event | 10.66 [3.90;17.43] | | |
| Coronary event | 14.52 [5.27;23.78] | | |

Discussion

Following the statement of the AHA for the assessment of the value of novel risk markers (Hlatky M A, et al. Circulation. 2009; 119:2408-2416), we have validated the association between a multi-locus GRS and the incidence of CVD and CHD events in a population-based prospective cohort. Furthermore, we have also shown the capacity of this GRS when added to the Framingham calibrated risk function to improve the prediction of CVD and CHD events, particularly in those individuals with intermediate risk.

Prospective Validation of the Association Between A Novel Multi-Locus Genetic Risk Score and CVD or CHD Events We report that a multi-locus GRS, composed by genetic variants mostly identified by GWAS, and unrelated to classical cardiovascular risk factors, is linearly and directly associated with the incidence of CVD and CHD events in the Regicor cohort. We also confirmed that the effect sizes for these variants are approximately 10% increased risk for CVD and CHD per unit of the GRS and that they were independent of familial history of CHD.

This effect size is smaller than that reported in discovery case-control studies, which is likely due to the tendency of case-control studies to overestimate the true effect size of the reported associations. This overestimation could also be explained by the "winner's curse" effect of the discovery studies, or the inclusion of an extreme definition of cases and controls in these studies.

Similarly to the classical CVD risk factors (D'Agostino R B, et al. JAMA. 2001;286(2):180-187), the effect size of the GRS seems to be comparable across populations with different absolute risk. Moreover, this effect size is similar to that of some classical cardiovascular risk factors (Wilson P W, et al. Circulation. 1998;97(18):1837-1847).

Our results are better that those reported by Paynter et al in a prospective cohort of 19,313 initially healthy white women in the Women's Genome Health Study (Paynter N P, et al. JAMA. 2010;303:631-637). In that study the authors constructed a multi-locus GRS with 11 SNPs associated with CHD in GWAS, which was not associated with the incidence of CVD.

Incremental Value of the Genetic Risk Score for CVD and CHD Risk Prediction

Our study is distinctive in the sense that we only included in our GRS those variants that were independent of classical risk factors in order to incorporate information complementary to that already included in the risk functions (Thanassoulis G, et al. Circulation. 2010;122:2323-2334). The inclusion of the GRS in the classical risk functions improved the classification of the individuals in the different risk categories, especially in those individuals with intermediate risk.

The assessment of the improvement of the predictive models should consider risk reclassification metrics such as NRI.

From a clinical perspective the low sensitivity of risk functions has already been documented in such a way that 50% of CHD events occur in the population with intermediate coronary risk (Marrugat J, et al. J Epidemiol Community Health. 2007;61:40-47). Therefore, the intermediate risk group may benefit the most from test oriented to stratify CHD risk more precisely. This would help to select the target population for more aggressive preventive measures. In our study we observed that the GRS improved the classification of individuals mainly in the intermediate risk categories.

In accordance to the results obtained in this study, the responsible consideration in the clinical practise of the information provided by our genetic risk score could be:

First, to identify patients at high cardiovascular risk. Several guidelines are available for the primary prevention of cardiovascular disease. If every person could receive the prevention therapy for which he or she is a candidate, myocardial infarcts could be reduced ≥60%, strokes could be reduced 30%, and everyone's life expectancies could be increased an average of 1.3 years and at a higher quality of life than currently experienced, (Circulation 2008;118:576). According to the work by Vancheri F et al (Eur J Inter Med 2009:20:601-606), in clinical practise, a great proportion of physicians dealing with primary cardiovascular prevention underclassify their patient's risk level. Moreover, when the decision to start pharmacological treatment was analysed in some cases the treatment was initiated in high risk patients (FRS >20%) while in others was initiated with FRS <20% decision being influenced by factors not directly related to the individual patient's risk. We strongly believe that the reclassification power of our genetic risk score should be used to identify patients located at moderate risk status by the classical risk functions who should be allocated at the high risk status and for whom preventive measurements should be implemented. Especially when most of the myocardial infarctions happen in patients being previously classified as moderate risk. For this reason we are very much encouraged by the excellent reclassification results we have obtained with the four SNPs genetic risk score in the moderate-high risk patients.

Second, to compare the cardiovascular risk without and with the genetic risk score. This is a similar concept to the relative risk promulgated by the European guidelines on cardiovascular disease (Eur J Cardiovas Prev Reha 2007;14 (Supple 2):e1-e40). Despite the value of their absolute risk, considering the genetic risk markers this value could be significantly higher. This is especially but not exclusively useful for young people or when the full development of the classical risk factors is not yet present or when the risk not associated to the classical risk factors is very much relevant. In the same line, it has been suggested that 10-year functions may underestimate the true risk burden, particularly in younger individuals underscoring the need for a long-term cardiovascular risk prediction models. This long-term models are also valuables for educational purposes since it can be used to teach the patients how their risk can be modified if he/she fulfil the treatment objectives. It is worthwhile to point out the great utility of the genetic scores in this field. Our genetic risk score conferred a risk comparable to other established risk factors such as plasma LDL cholesterol or systolic blood pressure.

Third, to adapt the intensity of the treatment or the treatment objectives to the level of risk. The intensity of any action against the risk factors should be adjusted to the severity of the risk. The reclassification of the patients at moderate risk could assist the physician to establish both the intensity and objectives of the treatment.

Fourth, to improve treatment compliance. On average, one seventh to one half of the patients do not comply with prescribed treatment regimens (Munger M A, et al. MedGenMed 2007; 9:58, Gamer J B Am J Cardiol 2010;105: 1495-1501). The knowledge of a genetic based disease has been proved to increase drug compliance (Umans-Eckenhausen M A, et al. Lancet 2001;357:165-168). Genetic risk scores could be of use to increase treatment compliance.

Conclusions

A multilocus genetic risk score (GRS) based on genetic variants unrelated to classical cardiovascular risk factors is direct and linearly associated with risk of CVD events in two different populations. This genetic score has been validated and documented the incremental value when added to standard risk markers using the Regicor and Framingham cohorts. These results point out the value of this validated genetic risk score over other genetic markers published so far.

List of preferred embodiments:
1. A method for a cardiovascular risk assessment in a subject comprising the steps of determining in a sample isolated from said subject the presence of polymorphisms at positions 27 within the nucleic acid sequences of SEQ ID NO:1 to 34, wherein the presence at position 27 of a C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO:12, A in SEQ ID NO:13, C in SEQ ID NO:14, G in SEQ ID NO:15, A in SEQ ID NO:16, A in SEQ ID NO:17, G in SEQ ID NO:18, C in SEQ ID NO:19, T in SEQ ID NO:20, A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID NO:31, C in SEQ ID NO:32, C in SEQ ID NO:33, and/or C in SEQ ID NO:34 is indicative of a risk of having a cardiovascular event.

2. A method for a reclassification of a subject to an improved risk assessment compared to that obtained using the scales/methods for such risk estimation such as, but not limited to Framingham, Regicor, Score, Procamor Qrisk comprising the steps of determining in a sample isolated from said subject the presence of polymorphisms at positions 27 within the nucleic acid sequences of SEQ ID NO:1 to 34, wherein the presence at position 27 of a C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO:12, A in SEQ ID NO:13, C in SEQ ID NO:14, G in SEQ ID NO:15, A in SEQ ID NO:16, A in SEQ ID NO:17, G in SEQ ID NO:18, C in SEQ ID NO:19, T in SEQ ID NO:20, A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID NO:31, C in SEQ ID NO:32, C in SEQ ID NO:33, and/or C in SEQ ID NO:34 is indicative of a risk of having a cardiovascular event.

3. A method for identifying a subject in need of cardiovascular therapy or in need of preventive cardiovascular therapy/measurements for a cardiovascular event comprising the steps of determining in a sample isolated from said subject the presence in at least one allele of polymorphisms at positions 27 within the nucleic acid sequences of SEQ ID NO:1 to 34, wherein the presence at position 27 of a C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO:12, A in SEQ ID NO:13, C in SEQ ID NO:14, G in SEQ ID NO:15, A in SEQ ID NO:16, A in SEQ ID NO: 17, G in SEQ ID NO:18, C in SEQ ID NO:19, T in SEQ ID NO:20, A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID NO:31, C in SEQ ID NO:32, C in SEQ ID NO:33, and/or C in SEQ ID NO:34 is indicative of having a decreased response to a cardiovascular therapy or of being in need of early and aggressive cardiovascular therapy or in need of prophylactic cardiovascular treatment.

4. A method to establish the therapeutical objectives of preventive and/or therapeutical treatments for a patient having a cardiovascular event or suspected of having a predisposition for a cardiovascular event wherein the patient and/or the therapeutical objectives are selected for said therapy based on the presence in a sample isolated from said subject of a polymorphism at position 27 in the nucleotide sequences of SEQ ID NO:1 to 34, wherein said polymorphism at said position 27 is C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO: 12, A in SEQ ID NO:13, C in SEQ ID NO:14, G in SEQ ID NO:15, A in SEQ ID NO:16, A in SEQ ID NO:17, G in SEQ ID NO:18, C in SEQ ID NO:19, T in SEQ ID NO:20, A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID N0:31, C in SEQ ID NO:32, C in SEQ ID NO:33, and/or C in SEQ ID NO:34.

5. A method of determining the probability of an individual of presenting a fatal or non-fatal myocardial infarction or angina in a 10 year period based on the presence of 1 to P classical risk factors and 1 to J polymorphisms at positions 27 in the nucleotide sequences of SEQ ID NO:1 to 34, wherein said polymorphisms at said positions 27 are selected from the group of C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO:12, A in SEQ ID NO:13, C in SEQ ID NO:14, G in SEQ ID NO:15, A in SEQ ID NO:16, A in SEQ ID NO:17, G in SEQ ID NO:18, C in SEQ ID NO:19, T in SEQ ID NO:20, A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID NO:31, C in SEQ ID NO:32, C in SEQ ID NO:33, and/or C in SEQ ID NO:34 using the formula:

$$1 - \hat{S}^{exp\left[\sum_{p=1}^{P} \beta_{CRF_p} * CRF_{p,i} + \sum_{j=1}^{J} \beta_{SNP_j} * SNP_{j,i} - \sum_{p=1}^{P} \beta_{CRF_p} * \overline{CRF_p} - \sum_{j=1}^{J} \beta_{SNP_j} * \overline{SNP_j}\right]}$$

wherein,
$\hat{S}$ is the mean survival free of coronary events at the population, $$\sum_{p=1}^{P}$$

is the summatory function along the P classical risk factors,
$\beta_{CRF_p}$ is the logarithm of hazard ratio corresponding to the classical coronary risk factor "p" as shown in table A,
$CRF_{p,i}$ is the value of each coronary risk factor "p" included in the equation for an individual "i", $$\sum_{j=1}^{J}$$

is the summatory function along the J genetic variants.
$\beta_{SNP_j}$ is the logarithm of hazard ratio corresponding to the genetic variant "j" as shown in table B.
$SNP_{j,i}$ is the number of risk alleles (0,1,2) for a specific genetic variant "j" included in the equation for an individual "i".
$\overline{CRF_p}$ is the average value for the classical risk factor "p" in the population.
$\overline{SNP_j}$ is the average risk allele number of copies for genetic variant "j" in the population.

6. A method of determining the probability of an individual of presenting a fatal or non-fatal myocardial infarction or angina in a 10 year period based on the presence of 1 to P different classical risk factors and 1 to Q different genetic variants wherein said genetic variant is a polymorphism at positions 27 in the nucleotide sequences of SEQ ID NO:1 to 34, wherein said polymorphism at said position 27 are selected from the group of C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO:12, A in SEQ ID NO:13, C in SEQ ID NO:14, G in SEQ ID NO:15, A in SEQ ID NO:16, A in SEQ ID NO:17, G in SEQ ID NO:18, C in SEQ ID NO:19, T in SEQ ID NO:20, A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID NO:31, C in SEQ ID NO:32, C in SEQ ID NO:33, and/or C in SEQ ID NO:34 using the formula:

$$1 - \hat{S}^{\exp\left[\sum_{p=1}^{P} \beta_{CRF_p} * CRF_{p,i} + \beta_{GRS} * GRS_i - \sum_{p=1}^{P} \beta_{CRF_p} * \overline{CRF_p} - \beta_{GRS} * \overline{GRS}\right]}$$

wherein
$\hat{S}$: mean survival free of coronary events at the population.
exp: natural exponentiation.

$$\sum_{p=1}^{P} \beta_{CRF_p} * CRF_{p,i}:$$

where
a.

$$\sum_{p=1}^{P}$$

summatory function along the P classical risk factors.
b. $\beta_{CRF_p}$ logarithm of hazard ratio corresponding to the classical coronary risk factor "p". The values of the β for each coronary risk factor "p" are shown in table C.
c. $CRF_{p,i}$: value of each coronary risk factor "p" included in the equation for an individual "i".
$\beta_{GRS}$: logarithm of hazard ratio corresponding to one unit increase in the value of the genetic risk score. The value of this $\beta_{GRS}$ is 0.104 with a range of values going from 0.010 to 0.500.
$\overline{CRF_p}$: average value for the classical risk factor "p" in the population. This average value will be adapted to the regional or national prevalence.
$\overline{GRS}$: mean value of the genetic risk score in the population.

7. A method of determining the probability of an individual of presenting a fatal or non-fatal myocardial infarction or angina in a 10 year period based on the presence of 1 to P different classical risk factors and 1 to Q different genetic variants wherein said genetic variant is a polymorphism at positions 27 in the nucleotide sequences of SEQ ID NO:1 to 34, wherein said polymorphism at said position 27 is selected from the group of C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, A in SEQ ID NO:11, G in SEQ ID NO:12, A in SEQ ID NO:13, C in SEQ ID NO:14, G in SEQ ID NO:15, A in SEQ ID NO:16, A in SEQ ID NO:17, G in SEQ ID NO:18, C in SEQ ID NO:19, T in SEQ ID NO:20, A in SEQ ID NO:21, G in SEQ ID NO:22, C in SEQ ID NO:23, C in SEQ ID NO:24, G in SEQ ID NO:25, C in SEQ ID NO:26, A in SEQ ID NO:27, C in SEQ ID NO:28, G in SEQ ID NO:29, T in SEQ ID NO:30, T in SEQ ID NO:31, C in SEQ ID NO:32, C in SEQ ID NO:33, and/or C in SEQ ID NO:34 using the steps of:
(i) compute the linear combination of risk factors wi using the function $$w_i = \beta_{chol} * (cholesterol_i - 6) + \beta_{SPB} * (SBP_i - 120) + \beta_{smoker} * current_i + \sum_{j=1}^{J} \beta_{SNP_j} * (SNP_{i,j} - \overline{SNP_{i,j}})$$

wherein
cholesterol: cholesterol level for the individual "i" in mmol/L.
$\beta_{chol}$: logarithm of hazard ratio corresponding to the cholesterol (Table E).
$SBP_i$: systolic blood pressure for the individual "i" in mmHg.
$\beta_{SBP}$: logarithm of hazard ratio corresponding to systolic blood pressure (Table E).
$current_i$: current smoking status for the individual "i" (1: current, 0: former/never).
$\beta_{smoker}$: logarithm of hazard ratio corresponding to systolic blood pressure (Table E).

$$\sum_{j=1}^{J} \beta_{SNP_j} * (SNP_{i,j} - \overline{SNP_{i,j}}):$$

e.

$$\sum_{j=1}^{J}$$

summary function along the J genetic variants.
f. $\beta_{SNP_j}$ logarithm of hazard ratio corresponding to the genetic variant "j". The possible range of values of the β for each genetic variant "j" is shown in table B.
g. $SNP_{j,i}$: number of risk alleles (0,1,2) for a specific genetic variant "j" included in the equation for an individual "i".
h. $\overline{SNP_j}$: average risk allele number of copies for genetic variant "j" in the population,
(ii) compute the baseline survival $S_0$ for a given age using the function $S_0(age)=\exp\{-\exp(\alpha)*(age-20)^p\}$ $S_0(age+10)=\exp\{-\exp(\alpha)*(age-10)^p\}$ wherein
α, p: shape and scale parameters of the weibull distribution wherein their values are shown in Table F (parameters)
exp: natural exponentiation,
(iii) compute 10 years survival $S_{10}(age)$ using the function $$S(age) = \{S_0(age)\}^{exp(w)}$$

$$S(age+10) = \{S_0(age+10)\}^{exp(w)}$$

$$S_{10}(age) = S(age+10)/S(age)$$

(iv) compute the probability of having the event during the 10 years follow-up $Risk_{10}(age)$ using the function, $$Risk_{10}(age) = 1 - S_{10}(age)$$

and
(v) compute the probability of having a cardiovascular event during the 10 years follow-up as the sum of coronary and non-coronary cardiovascular risk using the function $$CVDRisk_{10} = [CHDRisk_{10}(age)] + [Non\text{-}CHDRisk_{10}(age)]$$

8. A method as defined in any one of items 1 to 7 wherein the presence at position 27 is C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, G in SEQ ID NO:12, and A in SEQ ID NO:16.

9. A method as defined in any one of items 1 or 2 wherein the presence at position 27 is C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, A in SEQ ID NO:9, A in SEQ ID NO:10, G in SEQ ID NO:12, and A in SEQ ID NO:16.

10. A method as defined in any one of items 1 to 7 wherein the presence at position 27 is C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, and the A in SEQ ID NO:9, A in SEQ ID NO:10, G in SEQ ID NO:12, and A in SEQ ID NO:16, the latter four constituting haplotype B ALOX5 AP.

11. A method as defined in any one of items 1 to 7 wherein the presence at position 27 is C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, G in SEQ ID NO:8, and A in SEQ ID NO:9, A in SEQ ID NO:10, A in SEQ ID NO:11 and G in SEQ ID NO:12, the latter four constituting haplotype B ALOX5 AP.

12. A method as defined in any one of items 1 to 7 wherein the presence at position 27 is C in SEQ ID NO:1, C in SEQ ID NO:2, T in SEQ ID NO:3, C in SEQ ID NO:4, C in SEQ ID NO:5, C in SEQ ID NO:6, T in SEQ ID NO:7, and G in SEQ ID NO:8.

13. A method as defined in any one of items 1 to 7 wherein the presence at position 27 is C in SEQ ID NO:2, T in SEQ ID NO:3, C in SEQ ID NO:5, and G in SEQ ID NO:8.

14. A method as defined in any one of items 1 to 7 wherein the presence at position 27 is T in SEQ NO:31, C in SEQ NO:32, C in SEQ NO:33, and C in SEQ NO:34.

15. A method as defined in any of the items 1 to 4 and 9 to 14 wherein the cardiovascular event is selected from the group of fatal or non-fatal myocardial infarction, stroke, angina pectoris, transient ischemic attacks, peripheral arterial disease or a combination thereof.

16. A method as defined in any of items 1 to 15 further comprising determining one or more cardiovascular disease or disorder risk factor(s) selected from the group consisting of age, race, sex, body mass index, blood pressure, smoking status, low density lipoprotein (LDL)- or high density lipoprotein (HDL)-cholesterol level, systolic blood pressure, diastolic blood pressure, history of heart failure, diabetes, renal insufficiency, left ventricular hypertrophy, alcohol consumption history, smoking history, exercise history, diet, and family history of cardiovascular disease or disorder.

17. The method according to any one of items 1 to 16 wherein the sample is an oral tissue sample, scraping, or wash or a biological fluid sample, preferably saliva, urine or blood.

18. The method according to any one or more of items 1 to 17 wherein the presence or absence of the polynucleotide is identified by amplifying or failing to amplify an amplification product from the sample, wherein the amplification product is preferably digested with a restriction enzyme before analysis and/or wherein the SNP is identified by hybridizing the nucleic acid sample with a primer label which is a detectable moiety.

19. A method as defined in items 5 to 18 wherein a plurality of classical risk factors "p" are used being said plurality being selected from the group of:
Sex, age, Total cholesterol, HDL-cholesterol, blood pressure, diabetes and smoking,
Age, LDL-cholesterol, HDL-cholesterol, triglycerides, systolic blood pressure, family story of myocardial infarction and diabetes,
Sex, Log(age/10), total cholesterol/HDL-cholesterol, body mass index, family story of premature CVD, smoking, Townsend score of output area, systolic blood pressure, treatment for hypertension and interaction of systolic blood pressure and hypertension (SBP*HTN) treatment.

20. A method as defined in items 5 to 18 wherein the probability is determined for the period from 35 to 75 years of age of the subject.

21. A method as defined in items 5 to 18 wherein the probability is determined for the period from the actual age of the subject and until the age of 75 years of age of the subject.

22. A computer program or a computer-readable media containing means for carrying out a method as defined in any of items 1 to 21.

23. A kit comprising reagents for detecting the identity of the nucleotide at position 27 within a nucleic acid sequence selected from the group of SEQ ID NO:1 to 34.

24. A kit as defined in item 23 which comprises one or more primer pairs specific for the amplification of a region comprising at least position 27 within a nucleic acid sequence of SEQ ID NO:1 to 34.

25. A kit as defined in item 23 or 24 where the sequences selected are SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, and SEQ ID NO:16.

26. A kit as defined in item, 23 or 24 where the sequences selected are SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12.
27. A kit as defined in items 23 or 24 where the sequences selected are SEQ ID NO:1, SEQ ID NO:2, SEQ ID NO:3, SEQ ID NO:4, SEQ ID NO:5, SEQ ID NO:6, SEQ ID NO:7, SEQ ID NO:8, and sequences SEQ ID NO:9, SEQ ID NO:10, SEQ ID NO:12, and SEQ ID NO:16, the latter four constituting haplotype B ALOX5 AP.
28. A kit as defined in items 22 or 23 where the sequences selected are SEQ ID NO:1, SEQ ID NO:2, SEQ ID NO:3, SEQ ID NO:4, SEQ ID NO:5, SEQ ID NO:6, SEQ ID NO:7, SEQ ID NO:8, and the sequences SEQ ID NO:9, SEQ ID NO:10, SEQ ID NO:11, and SEQ ID NO:12, the latter four constituting haplotype B ALOX5 AP.
29. A kit as defined in items 23 or 24 where the sequences selected are SEQ ID NO:1, SEQ ID NO:2, SEQ ID NO:3, SEQ ID NO:4, SEQ ID NO:5, SEQ ID NO:6, SEQ ID NO:7, and SEQ ID NO:8.
30. A kit as defined in items 23 or 24 where the sequences selected are SEQ ID NO:2, SEQ ID NO:3, SEQ ID NO:5, and SEQ ID NO:8.
31. A kit as defined in items 21 or 24 or where the sequences selected are SEQ NO:31, SEQ NO:32, SEQ NO:33, and SEQ NO:34.

The invention claimed is:

1. A method comprising
   a) obtaining a biological sample isolated from a human subject,
   b) detecting the identity of at least the nucleotide at position 27 within the nucleic acid sequences of SEQ ID NOs: 2, 3, 5, and 8 in the biological sample isolated from the human subject to detect the presence of polymorphisms at least at said position, wherein detecting the identity of the nucleotide at position 27 within the nucleic acid sequences of SEQ ID NOs: 2, 3, 5, and 8 is by direct sequencing, primer extension, probe hybridization, nucleic acid amplification, or restriction endonuclease digestion and size separation,
   c) calculating a risk of the human subject having a cardiovascular disease or event, using a cardiovascular risk function, wherein calculating said risk comprises combining:
   a risk conferred by one or more classical coronary risk factors, based on respective weighted values of each of the one or more classical coronary risk factors for the human subject; and
   a risk conferred by the detected polymorphisms, based on a weighted number of risk alleles present for each polymorphism,
   d) selecting a human subject evaluated in step c) as having an elevated risk for preventative and/or therapeutic treatment for a cardiovascular disease or event, and
   e) administering to the selected human subject an agent with hypolipemic capabilities, an anticoagulant, an antiplatelet agent, a thrombolytic agent, an antithrombotic, an antiarrhythmic agent, an agent that prolongs repolarization, an antihypertensive agent, a vasodilator, an antihypertensive, a diuretic, an inotropic agent, and/or an antianginal agent.

2. The method as claimed in claim 1, wherein risk alleles comprise, at position 27, C in SEQ ID NO:2, T in SEQ ID NO:3, C in SEQ ID NO:5, and/or G in SEQ ID NO:8.

3. The method as claimed in claim 1, wherein the one or more classical coronary risk factors are selected from age, race, sex, body mass index, blood pressure, smoking status, low density lipoprotein (LDL)- and/or high density lipoprotein (HDL)-cholesterol level, total cholesterol level, systolic blood pressure, diastolic blood pressure, treatment for hypertension, history of heart failure, diabetes, renal insufficiency, left ventricular hypertrophy, alcohol consumption history, smoking history, exercise history, diet, and family history of cardiovascular disease or disorder, and wherein the method further comprising determining respective values for the one or more classical coronary risk factors for the human subject.

4. The method of claim 1, wherein the cardiovascular risk function is based on a risk function selected from an original Framingham function, an adapted Framingham function, a Regicor function, a Score function, a Procam function, or a Qrisk function.

5. The method as claimed in claim 1, wherein the agent with hypolipemic capabilities is an HMG-CoA reductase inhibitor or a bile acid sequestrant.

6. The method as claimed in claim 1, wherein the anti-arrhythmic agent is a sodium channel blocker, a beta-adrenergic blocker, a repolarization prolonging drug, or a calcium channel blocker.

7. The method as claimed in claim 1, wherein the anti-hypertensive agent is a sympatholytic, an alpha/beta blocker, an alpha blocker, an anti-angiotensin II agent, a beta blocker, a calcium channel blocker, or a vasodilator.

8. The method as claimed in claim 1, wherein the inotropic agent is a cardiac glycoside, a beta-adrenergic agonist or a phosphodiesterase inhibitor.

9. The method as claimed in claim 1, wherein the anti-anginal agents is an organonitrate, a calcium channel blocker, a beta blocker or a combination thereof.

10. The method of claim 1, wherein the cardiovascular risk function comprises the formula $$1 - \hat{S}^{exp\left[\sum_{p=1}^{P}\beta_{CRF_p}*CRF_{p,i} + \sum_{j=1}^{J}\beta_{SNP_j}*SNP_{j,i} - \sum_{p=1}^{P}\beta_{CRF_p}*\overline{CRF_p} - \sum_{j=1}^{J}\beta_{SNP_j}*\overline{SNP_j}\right]},$$

wherein
$\hat{S}$ is a mean survival free of coronary events in a population, $$\sum_{p=1}^{P}$$

is a summatory function along P classical coronary risk factors,
$\beta_{CRF_p}$ is a logarithm of hazard ratio corresponding to classical coronary risk factor "p",
$CRF_{p,i}$ is a value of classical coronary risk factor "p" included in the formula for the human subject "i", $$\sum_{j=1}^{J}$$

is a summatory function along J genetic variants including at least polymorphisms at position 27 within the nucleic acid sequences of SEQ ID NO: 2, 3, 5, and 8,
$\beta_{SNP_j}$ is a logarithm of hazard ratio corresponding to genetic variant "j",
$SNP_{j,i}$ is a number of risk alleles (0,1,2) of genetic variant "j" included in the formula for the human subject "i",
$\overline{CRF_p}$ is an average value for classical coronary risk factor "p" in the population, and
$\overline{SNP_j}$ is an average risk allele number of copies for genetic variant "j" in the population.

11. The method of claim 1, wherein the cardiovascular risk function comprises the formula $$1 - \hat{S}^{exp\left[\sum_{p=1}^{P}\beta_{CRF_p}*CRF_{p,i} + \beta_{CRS}*GRS_i - \sum_{p=1}^{P}\beta_{CRF_p}*\overline{CRF_p} - \beta_{CRS}*\overline{GRS}\right]},$$

wherein
$\hat{S}$ is a mean survival free of coronary events in a population,
$GRS_i$ is a genetic risk score defined as a weighted number of risk alleles for genetic variants included in the formula for the human subject "i", wherein the genetic variants include at least polymorphisms at position 27 within the nucleic acid sequences of SEQ ID NO: 2, 3, 5, and 8,
exp is natural exponentiation, $$\sum_{p=1}^{P}$$

is a summatory function along P classical coronary risk factors,
$\beta_{CRF_p}$ is a logarithm of hazard ratio corresponding to classical coronary risk factor "p",
$CRF_{p,i}$ is a value of coronary risk factor "p" included in the formula for the human subject "i",
$\beta_{GRS}$ is a logarithm of hazard ratio corresponding to one unit increase in the value of the genetic risk score,
$\overline{CRF_p}$ is an average value of classical coronary risk factor "p" in the population, and
$\overline{GRS}$ is a mean value of the genetic risk score in the population.

12. The method of claim 1, wherein c) comprises steps of:
(i) computing a linear combination of risk factors wi using the function $$w_i = \beta_{chol}*(cholesterol_i - 6) + \beta_{SPB}*(SBP_i - 120) + \beta_{smoker}*current_i + \sum_{j=1}^{J}\beta_{SNP_j}*(SNP_{i,j} - SNP_{i,j})$$

wherein
cholesterol is a cholesterol level for the human subject "i",
$\beta_{chol}$ is a logarithm of hazard ratio corresponding to the cholesterol,
$SBP_i$ is a systolic blood pressure for the human subject "i",
$\beta_{SBP}$ is a logarithm of hazard ratio corresponding to systolic blood pressure,
$current_i$ is a current smoking status for the individual "i",
$\beta_{smoker}$ is a logarithm of hazard ratio corresponding to current smoking status, $$\sum_{j=1}^{J}$$

is a summatory function along J genetic variants including at least polymorphisms at position 27 within the nucleic acid sequences of SEQ ID NO: 2, 3, 5, and 8,
$\beta_{SNP_j}$ is a logarithm of hazard ratio corresponding to genetic variant "j",
$SNP_{j,i}$ is a number of risk alleles (0,1,2) of genetic variant "j" included in the formula for the human subject "i", and
$\overline{SNP_j}$ is an average risk allele number of copies for genetic variant "j" in a population, (ii) computing the baseline survival $S_0$ for a given age using the function $S_0(\text{age}) = \exp\{\exp(\alpha)*(\text{age}-20)^p\}$ $S_0(\text{age}+10) = \exp\{-\exp(\alpha)*(\text{age}-10)^p\}$ wherein
    $\alpha$, p are shape and scale parameters of the weibull distribution, and
    exp is natural exponentiation, (iii) computing 10 years survival $S_{10}(\text{age})$ using the function $S(\text{age}) = \{S_0(\text{age})\}^{\exp(w)}$ $S(\text{age}+10) = \{S_0(\text{age}+10)\}^{\exp(w)}$ $S_{10}(\text{age}) = S(\text{age}+10)/S(\text{age})$, (iv) computing the probability of having an event during the 10 years follow-up $\text{Risk}_{10}(\text{age})$ using the function $\text{Risk}_{10}(\text{age}) = 1 - S_{10}(\text{age})$, and (v) computing the probability of having a cardiovascular event during the 10 years follow-up as the sum of coronary and non-coronary cardiovascular risk using the function $\text{CVDRisk}_{10} = [\text{CHDRisk}_{10}(\text{age})] + [\text{Non-CHDRisk}_{10}(\text{age})]$.

13. The method of claim 1, wherein the risk of the human subject having a cardiovascular disease or event is a probability of the human subject presenting a fatal or non-fatal myocardial infarction or angina in a 10 year period.

\* \* \* \* \*

UNITED STATES PATENT AND TRADEMARK OFFICE
CERTIFICATE OF CORRECTION

| | |
|---|---|
| PATENT NO. | : 11,814,673 B2 |
| APPLICATION NO. | : 14/236932 |
| DATED | : November 14, 2023 |
| INVENTOR(S) | : Eduardo Salas et al. |

It is certified that error appears in the above-identified patent and that said Letters Patent is hereby corrected as shown below:

In the Claims

Claim 1, at Column 59, Lines 59-61:
"based on respective weighted values of each of the one or more classical coronary risk factors for the human subject"

Should read:
-- based on respective weighted values of the one or more classical coronary risk factors for the human subject --

Signed and Sealed this
Ninth Day of January, 2024

Katherine Kelly Vidal
Director of the United States Patent and Trademark Office